United States Patent
Alten et al.

(10) Patent No.: US 10,526,407 B2
(45) Date of Patent: Jan. 7, 2020

(54) T CELL RECEPTORS AND IMMUNE THERAPY USING THE SAME

(71) Applicant: Immatics Biotechnologies GmbH, Tübingen (DE)

(72) Inventors: Leonie Alten, Tübingen (DE); Dominik Maurer, Mössingen (DE); Steffen Walter, Houston, TX (US); Sebastian Bunk, Tübingen (DE)

(73) Assignee: Immatics Biotechnologies GmbH, Tuebingen (DE)

( * ) Notice: Subject to any disclaimer, the term of this patent is extended or adjusted under 35 U.S.C. 154(b) by 0 days.

(21) Appl. No.: 16/035,300

(22) Filed: Jul. 13, 2018

(65) Prior Publication Data

US 2018/0319884 A1    Nov. 8, 2018

Related U.S. Application Data

(63) Continuation of application No. 15/677,651, filed on Aug. 15, 2017.

(60) Provisional application No. 62/376,632, filed on Aug. 18, 2016, provisional application No. 62/376,059, filed on Aug. 17, 2016.

(30) Foreign Application Priority Data

Aug. 17, 2016   (DE) .................... 10 2016 115 246

(51) Int. Cl.
| | | |
|---|---|---|
| C07K 16/28 | (2006.01) | |
| A61P 35/00 | (2006.01) | |
| C07K 14/725 | (2006.01) | |
| C07K 14/78 | (2006.01) | |
| C07K 16/18 | (2006.01) | |
| A61K 39/00 | (2006.01) | |

(52) U.S. Cl.
CPC .......... *C07K 16/2803* (2013.01); *A61P 35/00* (2018.01); *C07K 14/7051* (2013.01); *C07K 14/78* (2013.01); *C07K 16/18* (2013.01); *A61K 39/00* (2013.01); *A61K 2039/505* (2013.01); *C07K 2317/32* (2013.01); *C07K 2317/92* (2013.01); *C07K 2319/00* (2013.01)

(58) Field of Classification Search
None
See application file for complete search history.

(56) References Cited

U.S. PATENT DOCUMENTS 9,228,007 B1    1/2016  Kitchen et al.
2008/0219956 A1   9/2008  Russell et al.

FOREIGN PATENT DOCUMENTS

WO    2011113819 A2    9/2011
WO    2016011210 A2    1/2016

OTHER PUBLICATIONS

Popovic et al. (Blood. 2011; 118(4):946-954). (Year: 2011).*
Smith et al. (Br J Cancer. May 5, 2009;100(9):1452-64). (Year: 2009).*
Qiao et al. (Oncotarget. Oct. 6, 2015;6(30):29929-46). (Year: 2015).*
Sandberg et al., Proc Natl Acad Sci U S A. Feb. 8, 2005;102(6):2052-7. (Year: 2005).*
Qiao, J. "Stroma derived COL6A3 is a potential prognosis marker of colorectal carcinoma revealed by quantitative proteomics", Oncotarget (2015) 6 (30) 29929-46.
Database EMBL [Online]. Jul. 30, 2015 (Jul. 30, 2015) "*Homo sapiens* (human) partial T cell receptor alpha chain V-J-region", XP002774327, retrieved from EBI accession No. EMBL:BAS03272 Database accession No. BAS03272.
Database EMBL [Online]. Jul. 30, 2015 (Jul. 30, 2015) "*Homo sapiens* (human) partial T cell receptor beta chain V-D-J-region", XP002774328, retrieved from EBI accession No. EMBL:BAS04242 Database accession No. BAS04242.
Database EMBL [Online]. Jul. 30, 2015 (Jul. 30, 2015) "*Homo sapiens* (human) partial T cell receptor alpha chain V-J-region", XP002774329, retrieved from EBI accession No. EMBL:BAS03375 Database accession No. BAS03375.
Database EMBL [Online]. Jul. 30, 2015 (Jul. 30, 2015) "*Homo sapiens* (human) partial T cell receptor beta chain V-D-J-region", XP002774330, retrieved from EBI accession No. EMBL:BAS04067 Database accession No. BAS04067.
Database EMBL [Online]. Sep. 20, 2002 (Sep. 20, 2002) "*Homo sapiens* clone SC01 T cell receptor alpha mRNA partial cds", XP002774331, retrieved from EBI accession No. EMBL:AF532840 Database accession No. AF532840.
Database EMBL [Online]. Mar. 4, 2000 (Mar. 4, 2000) "*Homo sapiens* (human) partial T cell receptor beta", XP002774332, retrieved from EBI accession No. EMBL:AAD15181 Database accession No. AAD15181.
International Search Report for PCT/EP2017/066630, dated Oct. 20, 2017.
Faden et al., Hastings Cent Rep. Nov.-Dec. 2003;33(6):13-27 (Year: 2003).

(Continued)

*Primary Examiner* — Zachary S Skelding
(74) *Attorney, Agent, or Firm* — McBee Moore & Vanik IP, LLP

(57) ABSTRACT

The present invention pertains to antigen recognizing constructs against COL6A3 antigens. The invention in particular provides novel T cell receptor (TCR) based molecules which are selective and specific for the tumor expressed antigen COL6A3. The TCR of the invention, and COL6A3 antigen binding fragments derived therefrom, are of use for the diagnosis, treatment and prevention of COL6A3 expressing cancerous diseases. Further provided are nucleic acids encoding the antigen recognizing constructs of the invention, vectors comprising these nucleic acids, recombinant cells expressing the antigen recognizing constructs and pharmaceutical compositions comprising the compounds of the invention.

24 Claims, 12 Drawing Sheets
(6 of 12 Drawing Sheet(s) Filed in Color)
Specification includes a Sequence Listing.

(56) References Cited

OTHER PUBLICATIONS

Woodsworth et al., Genome Medicine 2013, 5:98 (Year: 2013).
Robins et al., Blood. 2009; 114:4099-4107 (Year: 2009).
Robert W. Bahr, Deputy Commissioner for Patent Examination Policy Memorandum of Feb. 22, 2018, 2 pages. (Year: 2018).
Janeway et al., Immunobiology, 5th Ed., Garland Science, pp. 106-108 and 260-263, (2001). (Year: 2001).
Garcia et al., Cell, vol. 122, 333-336, Aug. 12, 2005. (Year: 2005).
Portolano et al., J Immunol. Feb. 1, 1993; 150(3):880-7. (Year: 1993).
Goyarts et al. (Mol Immunol. Jul. 1998;35(10):593-607). (Year: 1998).
Communication issued pursuant to Rules 161(1) and 162 EPC in related European Patent Application No. 17739220.6. dated Mar. 26, 2019.
Piepenbrink, Kurt H. et al. (2013). "The basis for limited specificity and MHC restriction in a T cell receptor interface." Nature. 2013; 4:1948. doi:10.1038/ncomms2948.

\* cited by examiner

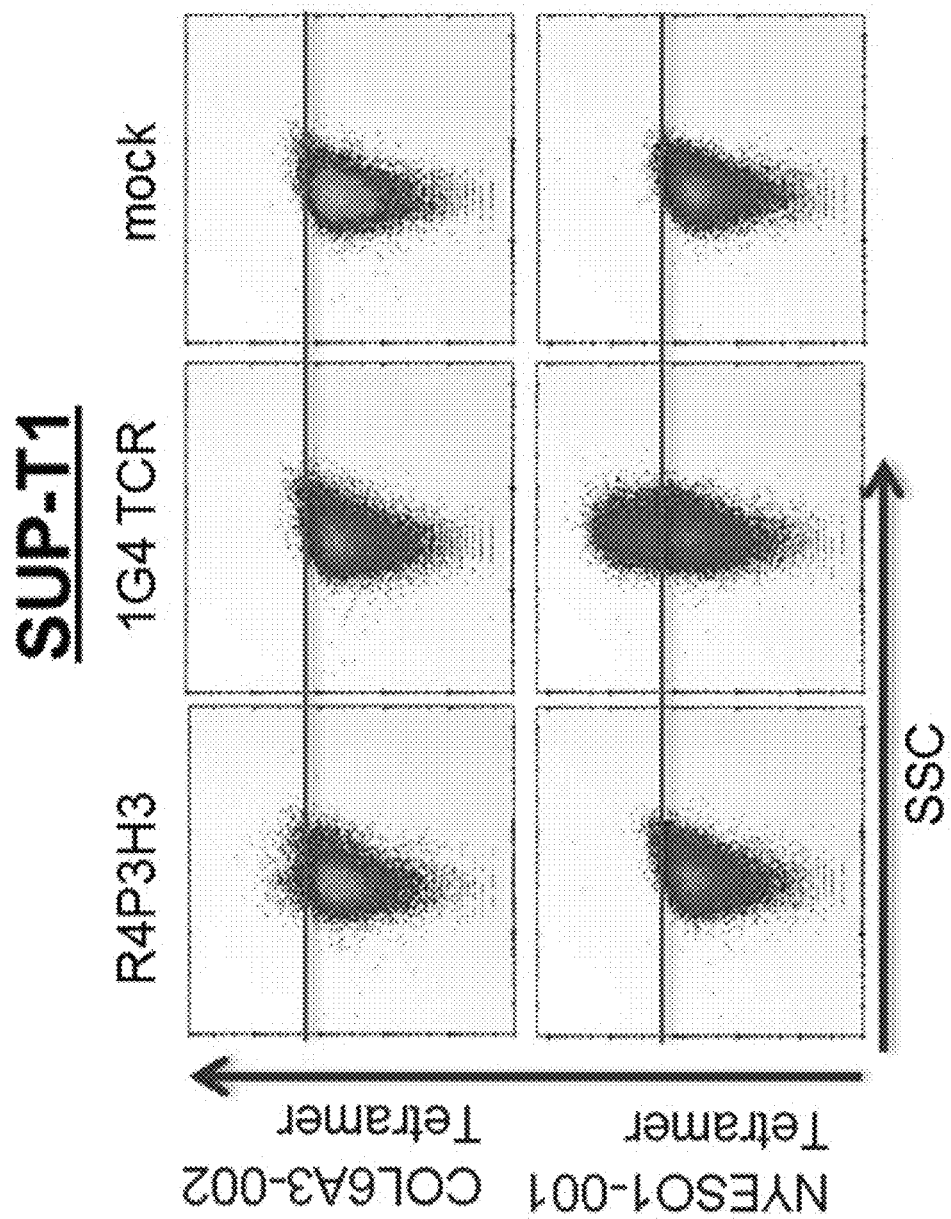

SEQUENCE LISTING

```
<160> NUMBER OF SEQ ID NOS: 74

<210> SEQ ID NO 1
<211> LENGTH: 6
<212> TYPE: PRT
<213> ORGANISM: Homo sapiens

<400> SEQUENCE: 1

Asp Arg Gly Ser Gln Ser
1               5

<210> SEQ ID NO 2
<211> LENGTH: 2
<212> TYPE: PRT
<213> ORGANISM: Homo sapiens

<400> SEQUENCE: 2

Ile Tyr
1

<210> SEQ ID NO 3
<211> LENGTH: 11
<212> TYPE: PRT
<213> ORGANISM: Homo sapiens

<400> SEQUENCE: 3

Cys Ala Val Asn Phe His Asp Lys Ile Ile Phe
1               5                   10

<210> SEQ ID NO 4
<211> LENGTH: 113
<212> TYPE: PRT
<213> ORGANISM: Homo sapiens

<400> SEQUENCE: 4

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Asn
```

<210> SEQ ID NO 5
<211> LENGTH: 141
<212> TYPE: PRT
<213> ORGANISM: Homo sapiens

<400> SEQUENCE: 5

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 6
<211> LENGTH: 271
<212> TYPE: PRT
<213> ORGANISM: Homo sapiens

<400> SEQUENCE: 6

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Asn Phe His Asp Lys Ile Ile Phe Gly Lys Gly Thr Arg Leu His Ile
        115                 120                 125

Leu Pro Asn Ile Gln Asn Pro Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
            195                 200                 205

Asn Ser Ile Ile Pro Glu Asp Thr Phe Phe Pro Ser Pro Glu Ser Ser
            210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
                260                 265                 270

<210> SEQ ID NO 7
<211> LENGTH: 5
<212> TYPE: PRT
<213> ORGANISM: Homo sapiens

<400> SEQUENCE: 7

Ser Gly Asp Leu Ser
1               5

<210> SEQ ID NO 8
<211> LENGTH: 6
<212> TYPE: PRT
<213> ORGANISM: Homo sapiens

<400> SEQUENCE: 8

Tyr Tyr Asn Gly Glu Glu
1               5

<210> SEQ ID NO 9
<211> LENGTH: 13
<212> TYPE: PRT
<213> ORGANISM: Homo sapiens

<400> SEQUENCE: 9

Cys Ala Ser Ser Val Ala Ser Ala Tyr Gly Tyr Thr Phe
1               5                   10

<210> SEQ ID NO 10
<211> LENGTH: 114
<212> TYPE: PRT
<213> ORGANISM: Homo sapiens

<400> SEQUENCE: 10

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile His Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
                100                 105                 110

Ser Val

<210> SEQ ID NO 11
<211> LENGTH: 177
<212> TYPE: PRT
<213> ORGANISM: Homo sapiens

<400> SEQUENCE: 11

```
Glu Asp Leu Asn Lys Val Phe Pro Pro Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe
```

<210> SEQ ID NO 12
<211> LENGTH: 308
<212> TYPE: PRT
<213> ORGANISM: Homo sapiens

<400> SEQUENCE: 12

```
Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile His Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Val Ala Ser Ala Tyr Gly Tyr Thr Phe Gly Ser Gly Thr Arg Leu
        115                 120                 125

Thr Val Val Glu Asp Leu Asn Lys Val Phe Pro Pro Glu Val Ala Val
    130                 135                 140

Phe Glu Pro Ser Glu Ala Glu Ile Ser His Thr Gln Lys Ala Thr Leu
```

```
            145                 150                 155                 160
Val Cys Leu Ala Thr Gly Phe Phe Pro Asp His Val Glu Leu Ser Trp
                    165                 170                 175

Trp Val Asn Gly Lys Glu Val His Ser Gly Val Ser Thr Asp Pro Gln
                    180                 185                 190

Pro Leu Lys Glu Gln Pro Ala Leu Asn Asp Ser Arg Tyr Cys Leu Ser
                    195                 200                 205

Ser Arg Leu Arg Val Ser Ala Thr Phe Trp Gln Asn Pro Arg Asn His
                    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                    245                 250                 255

Trp Gly Arg Ala Asp Cys Gly Phe Thr Ser Val Ser Tyr Gln Gln Gly
                    260                 265                 270

Val Leu Ser Ala Thr Ile Leu Tyr Glu Ile Leu Leu Gly Lys Ala Thr
                    275                 280                 285

Leu Tyr Ala Val Leu Val Ser Ala Leu Val Leu Met Ala Met Val Lys
                    290                 295                 300

Arg Lys Asp Phe
305

<210> SEQ ID NO 13
<211> LENGTH: 6
<212> TYPE: PRT
<213> ORGANISM: Homo sapiens

<400> SEQUENCE: 13

Asp Arg Gly Ser Gln Ser
1               5

<210> SEQ ID NO 14
<211> LENGTH: 2
<212> TYPE: PRT
<213> ORGANISM: Homo sapiens

<400> SEQUENCE: 14

Ile Tyr
1

<210> SEQ ID NO 15
<211> LENGTH: 14
<212> TYPE: PRT
<213> ORGANISM: Homo sapiens

<400> SEQUENCE: 15

Cys Ala Ala Tyr Ser Gly Ala Gly Ser Tyr Gln Leu Thr Phe
1               5                   10

<210> SEQ ID NO 16
<211> LENGTH: 111
<212> TYPE: PRT
<213> ORGANISM: Homo sapiens

<400> SEQUENCE: 16

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
                20                  25                  30
```

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
50                      55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala
            100                 105                 110

<210> SEQ ID NO 17
<211> LENGTH: 141
<212> TYPE: PRT
<213> ORGANISM: Homo sapiens

<400> SEQUENCE: 17

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 18
<211> LENGTH: 274
<212> TYPE: PRT
<213> ORGANISM: Homo sapiens

<400> SEQUENCE: 18

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
50                      55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Ala
            100                 105                 110

Tyr Ser Gly Ala Gly Ser Tyr Gln Leu Thr Phe Gly Lys Gly Thr Lys
            115                 120                 125

Leu Ser Val Ile Pro Asn Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 19
<211> LENGTH: 5
<212> TYPE: PRT
<213> ORGANISM: Homo sapiens

<400> SEQUENCE: 19

Ser Gly Asp Leu Ser
1               5

<210> SEQ ID NO 20
<211> LENGTH: 6
<212> TYPE: PRT
<213> ORGANISM: Homo sapiens

<400> SEQUENCE: 20

Tyr Tyr Asn Gly Glu Glu
1               5

<210> SEQ ID NO 21
<211> LENGTH: 13
<212> TYPE: PRT
<213> ORGANISM: Homo sapiens

<400> SEQUENCE: 21

Cys Ala Ser Ser Val Glu Ser Ser Tyr Gly Tyr Thr Phe
1               5                   10

<210> SEQ ID NO 22
<211> LENGTH: 114
<212> TYPE: PRT
<213> ORGANISM: Homo sapiens

<400> SEQUENCE: 22

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
            35                  40                  45

Leu Ser Val Tyr Trp Tyr Gln Gln Ser Leu Asp Gln Gly Leu Gln Phe
 50                  55                  60

Leu Ile His Tyr Tyr Asn Gly Glu Glu Arg Ala Lys Gly Asn Ile Leu
 65                  70                  75                  80

Glu Arg Phe Ser Ala Gln Gln Phe Pro Asp Leu His Ser Glu Leu Asn
                 85                  90                  95

Leu Ser Ser Leu Glu Leu Gly Asp Ser Ala Leu Tyr Phe Cys Ala Ser
                100                 105                 110

Ser Val

<210> SEQ ID NO 23
<211> LENGTH: 177
<212> TYPE: PRT
<213> ORGANISM: Homo sapiens

<400> SEQUENCE: 23

Glu Asp Leu Asn Lys Val Phe Pro Pro Glu Val Ala Val Phe Glu Pro
 1               5                  10                  15

Ser Glu Ala Glu Ile Ser His Thr Gln Lys Ala Thr Leu Val Cys Leu
                 20                  25                  30

Ala Thr Gly Phe Phe Pro Asp His Val Glu Leu Ser Trp Trp Val Asn
             35                  40                  45

Gly Lys Glu Val His Ser Gly Val Ser Thr Asp Pro Gln Pro Leu Lys
 50                  55                  60

Glu Gln Pro Ala Leu Asn Asp Ser Arg Tyr Cys Leu Ser Ser Arg Leu
 65                  70                  75                  80

Arg Val Ser Ala Thr Phe Trp Gln Asn Pro Arg Asn His Phe Arg Cys
                 85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
            115                 120                 125

Ala Asp Cys Gly Phe Thr Ser Val Ser Tyr Gln Gln Gly Val Leu Ser
        130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 24
<211> LENGTH: 308
<212> TYPE: PRT
<213> ORGANISM: Homo sapiens

<400> SEQUENCE: 24

Met Gly Phe Arg Leu Leu Cys Cys Val Ala Phe Cys Leu Leu Gly Ala
 1               5                  10                  15

Gly Pro Val Asp Ser Gly Val Thr Gln Thr Pro Lys His Leu Ile Thr
                 20                  25                  30

Ala Thr Gly Gln Arg Val Thr Leu Arg Cys Ser Pro Arg Ser Gly Asp
             35                  40                  45

Leu Ser Val Tyr Trp Tyr Gln Gln Ser Leu Asp Gln Gly Leu Gln Phe
 50                  55                  60

```
Leu Ile Gln Tyr Tyr Asn Gly Glu Glu Arg Ala Lys Gly Asn Ile Leu
 65                  70                  75                  80

Glu Arg Phe Ser Ala Gln Gln Phe Pro Asp Leu His Ser Glu Leu Asn
                 85                  90                  95

Leu Ser Ser Leu Glu Leu Gly Asp Ser Ala Leu Tyr Phe Cys Ala Ser
            100                 105                 110

Ser Val Glu Ser Ser Tyr Gly Tyr Thr Phe Gly Ser Gly Thr Arg Leu
        115                 120                 125

Thr Val Val Glu Asp Leu Asn Lys Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Val Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Phe
305

<210> SEQ ID NO 25
<211> LENGTH: 6
<212> TYPE: PRT
<213> ORGANISM: Homo sapiens

<400> SEQUENCE: 25

Asp Arg Gly Ser Gln Ser
1               5

<210> SEQ ID NO 26
<211> LENGTH: 2
<212> TYPE: PRT
<213> ORGANISM: Homo sapiens

<400> SEQUENCE: 26

Ile Tyr
1

<210> SEQ ID NO 27
<211> LENGTH: 11
<212> TYPE: PRT
<213> ORGANISM: Homo sapiens

<400> SEQUENCE: 27
```

```
Cys Ala Val Lys Ala Gly Asn Gln Phe Tyr Phe
1               5                   10
```

<210> SEQ ID NO 28
<211> LENGTH: 112
<212> TYPE: PRT
<213> ORGANISM: Homo sapiens

<400> SEQUENCE: 28

```
Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110
```

<210> SEQ ID NO 29
<211> LENGTH: 141
<212> TYPE: PRT
<213> ORGANISM: Homo sapiens

<400> SEQUENCE: 29

```
Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140
```

<210> SEQ ID NO 30
<211> LENGTH: 271
<212> TYPE: PRT
<213> ORGANISM: Homo sapiens

<400> SEQUENCE: 30

```
Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
```

```
                20                  25                  30
Ser Val Pro Glu Gly Ala Ile Ala Ser Leu Asn Cys Thr Tyr Ser Asp
            35                  40                  45

Arg Gly Ser Gln Ser Phe Phe Trp Tyr Arg Gln Tyr Ser Gly Lys Ser
        50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Lys Ala Gly Asn Gln Phe Tyr Phe Gly Thr Gly Thr Ser Leu Thr Val
        115                 120                 125

Ile Pro Asn Ile Gln Asn Pro Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 31
<211> LENGTH: 5
<212> TYPE: PRT
<213> ORGANISM: Homo sapiens

<400> SEQUENCE: 31

Ser Gly His Val Ser
1               5

<210> SEQ ID NO 32
<211> LENGTH: 6
<212> TYPE: PRT
<213> ORGANISM: Homo sapiens

<400> SEQUENCE: 32

Phe Gln Asn Glu Ala Gln
1               5

<210> SEQ ID NO 33
<211> LENGTH: 16
<212> TYPE: PRT
<213> ORGANISM: Homo sapiens

<400> SEQUENCE: 33

Cys Ala Ser Ser Leu Leu Thr Ser Gly Gly Asp Asn Glu Gln Phe Phe
1               5                   10                  15
```

```
<210> SEQ ID NO 34
<211> LENGTH: 115
<212> TYPE: PRT
<213> ORGANISM: Homo sapiens

<400> SEQUENCE: 34

Met Gly Thr Arg Leu Leu Cys Trp Val Val Leu Gly Phe Leu Gly Thr
1               5                   10                  15

Asp His Thr Gly Ala Gly Val Ser Gln Ser Pro Arg Tyr Lys Val Ala
            20                  25                  30

Lys Arg Gly Gln Asp Val Ala Leu Arg Cys Asp Pro Ile Ser Gly His
        35                  40                  45

Val Ser Leu Phe Trp Tyr Gln Gln Ala Leu Gly Gln Gly Pro Glu Phe
    50                  55                  60

Leu Thr Tyr Phe Gln Asn Glu Ala Gln Leu Asp Lys Ser Gly Leu Pro
65                  70                  75                  80

Ser Asp Arg Phe Phe Ala Glu Arg Pro Glu Gly Ser Val Ser Thr Leu
                85                  90                  95

Lys Ile Gln Arg Thr Gln Gln Glu Asp Ser Ala Val Tyr Leu Cys Ala
            100                 105                 110

Ser Ser Leu
        115

<210> SEQ ID NO 35
<211> LENGTH: 179
<212> TYPE: PRT
<213> ORGANISM: Homo sapiens

<400> SEQUENCE: 35

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 36
<211> LENGTH: 314
```

```
<212> TYPE: PRT
<213> ORGANISM: Homo sapiens

<400> SEQUENCE: 36

Met Gly Thr Arg Leu Leu Cys Trp Val Val Leu Gly Phe Leu Gly Thr
1               5                   10                  15

Asp His Thr Gly Ala Gly Val Ser Gln Ser Pro Arg Tyr Lys Val Ala
            20                  25                  30

Lys Arg Gly Gln Asp Val Ala Leu Arg Cys Asp Pro Ile Ser Gly His
        35                  40                  45

Val Ser Leu Phe Trp Tyr Gln Gln Ala Leu Gly Gln Gly Pro Glu Phe
    50                  55                  60

Leu Thr Tyr Phe Gln Asn Glu Ala Gln Leu Asp Lys Ser Gly Leu Pro
65                  70                  75                  80

Ser Asp Arg Phe Phe Ala Glu Arg Pro Glu Gly Ser Val Ser Thr Leu
                85                  90                  95

Lys Ile Gln Arg Thr Gln Gln Glu Asp Ser Ala Val Tyr Leu Cys Ala
            100                 105                 110

Ser Ser Leu Leu Thr Ser Gly Gly Asp Asn Glu Gln Phe Phe Gly Pro
        115                 120                 125

Gly Thr Arg Leu Thr Val Leu Glu Asp Leu Lys Asn Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Ser Arg Gly
305                 310

<210> SEQ ID NO 37
<211> LENGTH: 6
<212> TYPE: PRT
<213> ORGANISM: Homo sapiens

<400> SEQUENCE: 37

Asp Ser Ala Ile Tyr Asn
1               5

<210> SEQ ID NO 38
<211> LENGTH: 3
```

```
<212> TYPE: PRT
<213> ORGANISM: Homo sapiens

<400> SEQUENCE: 38

Ile Gln Ser
1

<210> SEQ ID NO 39
<211> LENGTH: 15
<212> TYPE: PRT
<213> ORGANISM: Homo sapiens

<400> SEQUENCE: 39

Cys Ala Val Arg Pro Thr Ser Gly Gly Ser Tyr Ile Pro Thr Phe
1               5                   10                  15

<210> SEQ ID NO 40
<211> LENGTH: 112
<212> TYPE: PRT
<213> ORGANISM: Homo sapiens

<400> SEQUENCE: 40

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

<210> SEQ ID NO 41
<211> LENGTH: 141
<212> TYPE: PRT
<213> ORGANISM: Homo sapiens

<400> SEQUENCE: 41

Tyr Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
            115                 120                 125
```

```
Gly Phe Asn Leu Leu Met Thr Leu Arg Leu Trp Ser Ser
            130                 135                 140
```

<210> SEQ ID NO 42
<211> LENGTH: 274
<212> TYPE: PRT
<213> ORGANISM: Homo sapiens

<400> SEQUENCE: 42

```
Met Glu Thr Leu Leu Gly Leu Leu Ile Leu Trp Leu Gln Leu Gln Trp
  1               5                  10                  15

Val Ser Ser Lys Gln Glu Val Thr Gln Ile Pro Ala Ala Leu Ser Val
             20                  25                  30

Pro Glu Gly Glu Asn Leu Val Leu Asn Cys Ser Phe Thr Asp Ser Ala
         35                  40                  45

Ile Tyr Asn Leu Gln Trp Phe Arg Gln Asp Pro Gly Lys Gly Leu Thr
     50                  55                  60

Ser Leu Leu Leu Ile Gln Ser Ser Gln Arg Glu Gln Thr Ser Gly Arg
 65                  70                  75                  80

Leu Asn Ala Ser Leu Asp Lys Ser Ser Gly Arg Ser Thr Leu Tyr Ile
                 85                  90                  95

Ala Ala Ser Gln Pro Gly Asp Ser Ala Thr Tyr Leu Cys Ala Val Arg
            100                 105                 110

Pro Thr Ser Gly Gly Ser Tyr Ile Pro Thr Phe Gly Arg Gly Thr Ser
        115                 120                 125

Leu Ile Val His Pro Tyr Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser
```

<210> SEQ ID NO 43
<211> LENGTH: 5
<212> TYPE: PRT
<213> ORGANISM: Homo sapiens

<400> SEQUENCE: 43

```
Met Asn His Glu Tyr
  1               5
```

<210> SEQ ID NO 44
<211> LENGTH: 6

```
<212> TYPE: PRT
<213> ORGANISM: Homo sapiens

<400> SEQUENCE: 44

Ser Val Gly Ala Gly Ile
1               5

<210> SEQ ID NO 45
<211> LENGTH: 14
<212> TYPE: PRT
<213> ORGANISM: Homo sapiens

<400> SEQUENCE: 45

Cys Ala Ser Ser Tyr Val Gly Asn Thr Gly Glu Leu Phe Phe
1               5                   10

<210> SEQ ID NO 46
<211> LENGTH: 114
<212> TYPE: PRT
<213> ORGANISM: Homo sapiens

<400> SEQUENCE: 46

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
                20                  25                  30

Lys Thr Gly Gln Ser Met Thr Leu Gln Cys Ala Gln Asp Met Asn His
            35                  40                  45

Glu Tyr Met Ser Trp Tyr Arg Gln Asp Pro Gly Met Gly Leu Arg Leu
        50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr

<210> SEQ ID NO 47
<211> LENGTH: 179
<212> TYPE: PRT
<213> ORGANISM: Homo sapiens

<400> SEQUENCE: 47

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Tyr Pro Asp His Val Glu Leu Ser Trp Trp Val Asn
            35                  40                  45

Gly Lys Glu Val His Ser Gly Val Ser Thr Asp Pro Gln Pro Leu Lys
        50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110
```

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 48
<211> LENGTH: 311
<212> TYPE: PRT
<213> ORGANISM: Homo sapiens

<400> SEQUENCE: 48

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
                20                  25                  30

Lys Thr Gly Gln Ser Met Thr Leu Gln Cys Ala Gln Asp Met Asn His
            35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Val Gly Asn Thr Gly Glu Leu Phe Phe Gly Glu Gly Ser Arg
        115                 120                 125

Leu Thr Val Leu Glu Asp Leu Lys Asn Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
    195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
    275                 280                 285

Thr Leu Tyr Ala Val Leu Val Ser Ala Leu Val Leu Met Ala Met Val
290                 295                 300

```
Lys Arg Lys Asp Ser Arg Gly
305                 310

<210> SEQ ID NO 49
<211> LENGTH: 9
<212> TYPE: PRT
<213> ORGANISM: Homo sapiens

<400> SEQUENCE: 49

Ala Leu Leu Asp Gly Arg Val Gln Leu
1               5

<210> SEQ ID NO 50
<211> LENGTH: 9
<212> TYPE: PRT
<213> ORGANISM: Homo sapiens

<400> SEQUENCE: 50

Arg Leu Leu Asp Gly Ala Phe Lys Leu
1               5

<210> SEQ ID NO 51
<211> LENGTH: 9
<212> TYPE: PRT
<213> ORGANISM: Homo sapiens

<400> SEQUENCE: 51

Ile Leu Leu Asp Gly Ser Ala Ser Val
1               5

<210> SEQ ID NO 52
<211> LENGTH: 9
<212> TYPE: PRT
<213> ORGANISM: Homo sapiens

<400> SEQUENCE: 52

Phe Leu Leu Asp Gly Ser Glu Arg Leu
1               5

<210> SEQ ID NO 53
<211> LENGTH: 10
<212> TYPE: PRT
<213> ORGANISM: Homo sapiens

<400> SEQUENCE: 53

Phe Leu Phe Asp Gly Ser Ala Asn Leu Val
1               5                   10

<210> SEQ ID NO 54
<211> LENGTH: 9
<212> TYPE: PRT
<213> ORGANISM: Homo sapiens

<400> SEQUENCE: 54

Phe Leu Phe Asp Gly Ser Ala Asn Leu
1               5

<210> SEQ ID NO 55
<211> LENGTH: 9
<212> TYPE: PRT
<213> ORGANISM: Homo sapiens

<400> SEQUENCE: 55

Phe Leu Leu Asp Gly Ser Glu Gly Val
1               5
```

```
<210> SEQ ID NO 56
<211> LENGTH: 9
<212> TYPE: PRT
<213> ORGANISM: Homo sapiens

<400> SEQUENCE: 56

Phe Leu Leu Asp Gly Ser Asn Ser Val
1               5

<210> SEQ ID NO 57
<211> LENGTH: 9
<212> TYPE: PRT
<213> ORGANISM: Homo sapiens

<400> SEQUENCE: 57

Phe Leu Leu Asp Gly Ser Ser Arg Leu
1               5

<210> SEQ ID NO 58
<211> LENGTH: 9
<212> TYPE: PRT
<213> ORGANISM: Homo sapiens

<400> SEQUENCE: 58

Phe Leu Leu Asp Gly Ser Ala Asn Val
1               5

<210> SEQ ID NO 59
<211> LENGTH: 9
<212> TYPE: PRT
<213> ORGANISM: Homo sapiens

<400> SEQUENCE: 59

Ala Leu Leu Asp Gly Ser Ala Asn Val
1               5

<210> SEQ ID NO 60
<211> LENGTH: 9
<212> TYPE: PRT
<213> ORGANISM: Homo sapiens

<400> SEQUENCE: 60

Phe Ala Leu Asp Gly Ser Ala Asn Val
1               5

<210> SEQ ID NO 61
<211> LENGTH: 9
<212> TYPE: PRT
<213> ORGANISM: Homo sapiens

<400> SEQUENCE: 61

Phe Leu Ala Asp Gly Ser Ala Asn Val
1               5

<210> SEQ ID NO 62
<211> LENGTH: 9
<212> TYPE: PRT
<213> ORGANISM: Homo sapiens

<400> SEQUENCE: 62

Phe Leu Leu Ala Gly Ser Ala Asn Val
1               5
```

<210> SEQ ID NO 63
<211> LENGTH: 9
<212> TYPE: PRT
<213> ORGANISM: Homo sapiens

<400> SEQUENCE: 63

Phe Leu Leu Asp Ala Ser Ala Asn Val
1               5

<210> SEQ ID NO 64
<211> LENGTH: 9
<212> TYPE: PRT
<213> ORGANISM: Homo sapiens

<400> SEQUENCE: 64

Phe Leu Leu Asp Gly Ala Ala Asn Val
1               5

<210> SEQ ID NO 65
<211> LENGTH: 9
<212> TYPE: PRT
<213> ORGANISM: Homo sapiens

<400> SEQUENCE: 65

Phe Leu Leu Asp Gly Ser Gly Asn Val
1               5

<210> SEQ ID NO 66
<211> LENGTH: 9
<212> TYPE: PRT
<213> ORGANISM: Homo sapiens

<400> SEQUENCE: 66

Phe Leu Leu Asp Gly Ser Ala Ala Val
1               5

<210> SEQ ID NO 67
<211> LENGTH: 9
<212> TYPE: PRT
<213> ORGANISM: Homo sapiens

<400> SEQUENCE: 67

Phe Leu Leu Asp Gly Ser Ala Asn Ala
1               5

<210> SEQ ID NO 68
<211> LENGTH: 9
<212> TYPE: PRT
<213> ORGANISM: Homo sapiens

<400> SEQUENCE: 68

Ser Leu Leu Met Trp Ile Thr Gln Val
1               5

<210> SEQ ID NO 69
<211> LENGTH: 21
<212> TYPE: PRT
<213> ORGANISM: Homo sapiens

<400> SEQUENCE: 69

Met Lys Ser Leu Arg Val Leu Leu Val Ile Leu Trp Leu Gln Leu Ser
1               5                   10                  15

Trp Val Trp Ser Gln
            20

```
<210> SEQ ID NO 70
<211> LENGTH: 19
<212> TYPE: PRT
<213> ORGANISM: Homo sapiens

<400> SEQUENCE: 70

Met Gly Phe Arg Leu Leu Cys Cys Val Ala Phe Cys Leu Leu Gly Ala
1               5                   10                  15

Gly Pro Val

<210> SEQ ID NO 71
<211> LENGTH: 21
<212> TYPE: PRT
<213> ORGANISM: Homo sapiens

<400> SEQUENCE: 71

Met Lys Ser Leu Arg Val Leu Leu Val Ile Leu Trp Leu Gln Leu Ser
1               5                   10                  15

Trp Val Trp Ser Gln
                20

<210> SEQ ID NO 72
<211> LENGTH: 19
<212> TYPE: PRT
<213> ORGANISM: Homo sapiens

<400> SEQUENCE: 72

Met Gly Phe Arg Leu Leu Cys Cys Val Ala Phe Cys Leu Leu Gly Ala
1               5                   10                  15

Gly Pro Val

<210> SEQ ID NO 73
<211> LENGTH: 21
<212> TYPE: PRT
<213> ORGANISM: Homo sapiens

<400> SEQUENCE: 73

Met Lys Ser Leu Arg Val Leu Leu Val Ile Leu Trp Leu Gln Leu Ser
1               5                   10                  15

Trp Val Trp Ser Gln
                20

<210> SEQ ID NO 74
<211> LENGTH: 19
<212> TYPE: PRT
<213> ORGANISM: Homo sapiens

<400> SEQUENCE: 74

Met Gly Thr Arg Leu Leu Cys Trp Val Val Leu Gly Phe Leu Gly Thr
1               5                   10                  15

Asp His Thr
```

T CELL RECEPTORS AND IMMUNE THERAPY USING THE SAME

CROSS REFERENCE TO RELATED APPLICATIONS

This application is continuation of U.S. patent application Ser. No. 15/677,651, filed 15 Aug. 2017 which claims priority to U.S. Provisional Application No. 62/376,632, filed 18 Aug. 2016, U.S. Provisional Application No. 62/376,059, filed 17 Aug. 2016, and German Application No. 102016115246.3, filed 17 Aug. 2016. The contents of each of the aforementioned applications is herein incorporated by reference in their entirety.

This application also is related to PCT/EP2017/066630 filed 4 Jul. 2017, the content of which is incorporated herein by reference in its entirety.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "2912919-074003_Sequence_Listing_ST25.txt" created on 6 Jul. 2018, and 48,348 bytes in size) is submitted concurrently with the instant application, and the entire contents of the Sequence Listing are incorporated herein by reference.

FIELD OF THE INVENTION

The present invention pertains to antigen recognizing constructs against COL6A3 antigens. The invention in particular provides novel T cell receptor (TCR) based molecules which are selective and specific for the tumor expressed antigen COL6A3. The TCR of the invention, and COL6A3 antigen binding fragments derived therefrom, are of use for the diagnosis, treatment and prevention of COL6A3 expressing cancerous diseases. Further provided are nucleic acids encoding the antigen recognizing constructs of the invention, vectors comprising these nucleic acids, recombinant cells expressing the antigen recognizing constructs and pharmaceutical compositions comprising the compounds of the invention.

BACKGROUND OF THE INVENTION

The collagens are a superfamily of proteins that play a role in maintaining the integrity of various tissues. Collagens are extracellular matrix proteins and have a triple-helical domain as their common structural element. Collagen VI is a major structural component of microfibrils. The basic structural unit of collagen VI is a heterotrimer of the alpha 1(VI), alpha 2(VI), and alpha 3(VI) collagen chains. The alpha 1(VI) and alpha 2(VI) chains are encoded by the COL6A1 and COL6A2 genes, respectively. The protein encoded by the COL6A3 gene is the alpha 3 subunit of type VI collagen (alpha 3(VI) collagen chain) (Bertini et al., 2002 Eur. J. Paediatr. Neurol 6:193-8). COL6A3's gene expression was previously shown to be associated with the progression of breast cancer and was elevated in colon cancer (Smith M J, et al. "Analysis of differential gene expression in colorectal cancer and stroma using fluorescence-activated cell sorting purification" British journal of cancer. 2009; 100:1452-1464; Tilman G et al "Human periostin gene expression in normal tissues, tumors and melanoma: evidences for periostin production by both stromal and melanoma cells" Mol Cancer. 2007; 6:80) and as a prognosis marker of colorectal carcinoma (Qiao J et al. "Stroma derived COL6A3 is a potential prognosis marker of colorectal carcinoma revealed by quantitative proteomics" Oncotarget. 2015 Oct. 6; 6(30): 29929-29946). COL6A3 gene locates 2q37 in the human genome and contains 44 exons. The COL6A3 protein has 3177 amino acids and contains 12 Von Willebrand factor type A (vWA) domains, one fibronectin type 3 domain and one BPTI/Kunitz family of serine protease inhibitors (KU) domain.

T-cell based immunotherapy targets represent peptide epitopes derived from tumor-associated or tumor-specific proteins, which are presented by molecules of the major histocompatibility complex (MHC). These tumor associated antigens (TAAs) can be peptides derived from all protein classes, such as enzymes, receptors, transcription factors, etc. which are expressed and, as compared to unaltered cells of the same origin, usually up-regulated in cells of the respective tumor.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defective ribosomal products (DRiPs) located in the cytosol, play an important role in this response. The MHC-molecules of the human are also designated as human leukocyte-antigens (HLA).

A TCR is a heterodimeric cell surface protein of the immunoglobulin super-family, which is associated with invariant proteins of the CD3 complex involved in mediating signal transduction. TCRs exist in $\alpha\beta$ and $\gamma\delta$ forms, which are structurally similar but have quite distinct anatomical locations and probably functions. The extracellular portion of native heterodimeric $\alpha\beta$TCR consists of two polypeptides, each of which has a membrane-proximal constant domain, and a membrane-distal variable domain. Each of the constant and variable domains includes an intra-chain disulfide bond. The variable domains contain the highly polymorphic loops analogous to the complementarity determining regions (CDRs) of antibodies. The use of TCR gene therapy overcomes a number of current hurdles. It allows equipping patients' own T cells with desired specificities and generation of sufficient numbers of T cells in a short period of time, avoiding their exhaustion. The TCR will be transduced into central memory T cells or T cells with stem cell characteristics, which may ensure better persistence and function upon transfer. TCR-engineered T cells will be infused into cancer patients rendered lymphopenic by chemotherapy or irradiation, allowing efficient engraftment but inhibiting immune suppression.

SUMMARY OF THE INVENTION

While advances have been made in the development of molecular-targeting drugs for cancer therapy, there remains a need in the art to develop new anti-cancer agents that specifically target molecules highly specific to cancer cells. The present description addresses that need by providing novel COL6A3 TCRs, respective recombinant TCR constructs, nucleic acids, vectors and host cells that specifically bind COL6A3 epitope(s) as disclosed; and methods of using such molecules in the treatment of cancer.

The object of the invention is solved in a first aspect by an antigen recognizing construct comprising at least one complementary determining region (CDR) 3 having at least 50%, 60%, 70%, 80%, 90%, 95%, 98%, 99%, or preferably 100% sequence identity to an amino acid sequence selected from SEQ ID Nos. 3, 9, 15, 21, 27 and 33.

In another additional or alternative embodiment, the antigen recognizing construct may further comprise a CDR1 and/or a CDR2 domain sequence. Within the variable domain, CDR1 and CDR2 are found in the variable (V) region of a polypeptide chain, and CDR3 includes some of V, all of diversity (D) and joining (J) regions. CDR3 is the most variable and is the main CDR responsible for specifically and selectively recognizing an antigen. CDR1 and CDR2 sequences may be selected from a CDR sequence of a human variable chain allele.

Native alpha-beta heterodimeric TCRs have an alpha chain and a beta chain. Each chain comprises variable, joining and constant regions, and the beta chain also usually contains a short diversity region between the variable and joining regions, but this diversity region is often considered as part of the joining region. Each variable region comprises three CDRs (Complementarity Determining Regions) embedded in a framework sequence, one being the hypervariable region named CDR3. There are several types of alpha chain variable (Vα) regions and several types of beta chain variable (Vβ) regions distinguished by their framework, CDR1 and CDR2 sequences, and by a partly defined CDR3 sequence. The Vα types are referred to in IMGT nomenclature by a unique TRAV number, Vβ types are referred to by a unique TRBV number.

Therefore, in one additional or alternative embodiment the antigen recognizing construct of the invention comprises CDR1, CDR2 and CDR3 sequences in a combination as provided in table 1 herein below, which display the respective variable chain allele together with the CDR3 sequence. Therefore, preferred are antigen recognizing constructs of the invention which comprise at least one, preferably, all three CDR sequences CDR1, CDR2 and CDR3. Preferably, an antigen recognizing construct of the invention comprises the respective CDR1 to CDR3 of one individual herein disclosed TCR variable region of the invention.

The term "specificity" or "antigen specificity" or "specific for" a given antigen, as used herein means that the antigen recognizing construct can specifically bind to said antigen, preferably a COL6A3 antigen, more preferably with high avidity, when said antigen is by HLA, preferably HLA A2. For example, a TCR, as antigen recognizing construct, may be considered to have "antigenic specificity" for COL6A3 antigens, if T cells expressing the TCR and contacted with a COL6A3 presenting HLA secrete at least about 200 pg/ml or more (e.g., 250 pg/ml or more, 300 pg/ml or more, 400 pg/ml or more, 500 pg/ml or more, 600 pg/ml or more, 700 pg/ml or more, 1000 pg ml or more, 2,000 pg/ml or more, 2,500 pg/ml or more, 5,000 pg/ml or more) of interferon γ (IFN-γ) upon co-culture with target cells pulsed with a low concentration of a COL6A3 antigen, such as the COL6A3 epitopes and antigens provided herein below (e.g., about 10-11 mol/l, 10-10 mol/l, 10-9 mol/l, 10-8 mol/l, 10-7 mol/l, 10-6 mol/l, 10-5 mol/l). Alternatively, or additionally, a TCR may be considered to have "antigenic specificity" for COL6A3, if T cells expressing the TCR secrete at least twice as much IFN-γ as the untransduced background level of IFN-γ upon co-culture with target cells pulsed with a low concentration of COL6A3 antigens. Such a "specificity" as described above can—for example—be analyzed with an ELISA.

In one alternative or additional embodiment of the invention, the antigen recognizing construct selectively binds to a COL6A3 antigen; preferably wherein the COL6A3 antigen is a protein epitope or peptide having an amino acid sequence shown in SEQ ID NO: 58 to 67, most preferably SEQ ID NO: 58, or a variant thereof, wherein the variant is an amino acid deletion, addition, insertion or substitution of not more than three, preferably two and most preferably not more than one amino acid position.

The term "selectivity" or "selective recognizing/binding" is understood to refer to the property of an antigen recognizing construct, such as a TCR or antibody, to selectively recognize or bind to preferably only one specific epitope and preferably shows no or substantially no cross-reactivity to another epitope. Preferably "selectivity" or "selective recognizing/binding" means that the antigen recognizing construct (e.g. a TCR) selectively recognizes or binds to preferably only one specific epitope and preferably shows no or substantially no cross-reactivity to another epitope, wherein said epitope is unique for one protein, such that the antigen recognizing construct shows no or substantially no cross-reactivity to another epitope and another protein.

The antigen recognizing construct according to the invention is preferably selected from an antibody, or derivative or fragment thereof, or a T cell receptor (TCR), or derivative or fragment thereof. A derivative or fragment of an antibody or TCR of the invention shall preferably retain the antigen binding/recognizing ability of the parent molecule, in particular its specificity and/or selectivity as explained above. Such binding functionality may be retained by the presence of a CDR3 region as defined herein.

In an embodiment of the invention, the inventive TCRs are able to recognize COL6A3 antigens in a major histocompatibility complex (MHC) class I-dependent manner "MHC class I-dependent manner," as used herein, means that the TCR elicits an immune response upon binding to COL6A3 antigens within the context of an MHC class I molecule. The MHC class I molecule can be any MHC class I molecule known in the art, e.g., HLA-A molecules. In a preferred embodiment of the invention, the MHC class I molecule is an HLA-A2 molecule.

The invention provides both single chain antigen recognizing construct and double chain recognizing constructs.

The invention in particular provides a TCR as antigen recognizing construct, or fragment or derivative thereof. The TCR preferably is of human, which is understood as being generated from a human TCR locus and therefore comprising human TCR sequences. Furthermore, the TCR of the invention may be characterized in that it is of human origin and specifically recognizes a COL6A3 antigen.

Another embodiment of the invention additionally or alternatively provides the antigen recognizing construct described above, which induces an immune response, preferably wherein the immune response is characterized by an increase in interferon (IFN) γ levels.

TCRs of the invention may be provided as single chain α or β, or γ and δ, molecules, or alternatively as double chain constructs composed of both the α and β chain, or γ and δ chain. The antigen recognizing construct of the invention may comprise a TCR α or γ chain; and/or a TCR β or δ chain; wherein the TCR α or γ chain comprises a CDR3 having at least 50%, 60%, 70%, 80%, 90%, 95%, 98%, 99%, or 100% sequence identity to an amino acid sequence selected from SEQ ID Nos. 3, 15, and 27, and/or wherein the TCR β or δ chain comprises a CDR3 having at least 50%, 60%, 70%, 80%, 90%, 95%, 98%, 99%, or 100% sequence identity to an amino acid sequence selected from SEQ ID Nos. 9, 21, and 33.

Most preferably, in some additional embodiments, wherein the disclosure refers to antigen recognizing constructs comprising any one, two or all of the CDR1 to CDR3 regions of the herein disclosed TCR chains (see table 1), such antigen recognizing constructs may be preferred, which comprise the respective CDR sequence having three, two, and preferably only one, modified amino acid residues. A modified amino acid residue may be selected from an amino acid insertion, deletion or substitution. Most preferred is that the three, two, preferably one modified amino acid residue is the first or last amino acid residue of the respective CDR sequence. If the modification is a substitution then it is preferable in some embodiments that the substitution is a conservative amino acid substitution.

If the antigen recognizing construct of the invention is composed of at least two amino acid chains, such as a double chain TCR, or antigen binding fragment thereof, the antigen recognizing construct may comprises in a first polypeptide chain the amino acid sequence according to SEQ ID NO: 3, and in a second polypeptide chain the amino acid sequence according to SEQ ID NO: 9; or in a first polypeptide chain the amino acid sequence according to SEQ ID NO: 15, and in a second polypeptide chain the amino acid sequence according to SEQ ID NO: 21; or in a first polypeptide chain the amino acid sequence according to SEQ ID NO: 27, and in a second polypeptide chain the amino acid sequence according to SEQ ID NO: 33. Any one of the aforementioned double chain TCR, or antigen binding fragments thereof, are preferred TCR of the present invention. In some embodiments, the CDR3 of the double chain TCR of the invention may be mutated. Mutations of the CDR3 sequences of SEQ ID NOs: 9 to 28 as provided above preferably include a substitution, deletion, addition, or insertion of not more than three, preferably two, and most preferably not more than one amino acid residue. In some embodiments, the first polypeptide chain may be a TCR α or γ chain, and the second polypeptide chain may be a TCR β or δ chain. Preferred is the combination of an αβ or γδ TCR.

The TCR, or the antigen binding fragment thereof, is in some embodiments composed of a TCR α and a TCR β chain, or γ and δ chain. Such a double chain TCR comprises within each chain variable regions, and the variable regions each comprise one CDR1, one CDR2 and one CDR3 sequence. The TCRs comprises the CDR1 to CDR3 sequences as comprised in the variable chain amino acid sequence of SEQ ID NO: 4 and SEQ ID NO: 10 (R4P1D10), or SEQ ID NO: 16 and SEQ ID NO: 22 (R4P3F9); or SEQ ID NO: 28 and SEQ ID NO: 34 (R4P3H3).

Some embodiments of the invention pertain to a TCR, or a fragment thereof, composed of a TCR α and a TCR β chain, wherein said TCR comprises the variable region sequences having at least 50%, 60%, 70%, 80%, 90%, 95%, 98%, 99%, or preferably 100% sequence identity to the amino acid sequence selected from the α and β chain according to SEQ ID NO: 4 and 10 respectively, or 16 and 22 respectively; or 28 and 34 respectively.

The inventive TCRs may further comprise a constant region derived from any suitable species, such as any mammal, e.g., human, rat, monkey, rabbit, donkey, or mouse. In an embodiment of the invention, the inventive TCRs further comprise a human constant region. In some preferred embodiments, the constant region of the TCR of the invention may be slightly modified, for example, by the introduction of heterologous sequences, preferably mouse sequences, which may increase TCR expression and stability.

Some embodiments of the invention pertain to a TCR, or a fragment thereof, composed of a TCR α and a TCR β chain, wherein said TCR comprises the constant region having at least 50%, 60%, 70%, 80%, 90%, 95%, 98%, 99%, or preferably 100% sequence identity to an amino acid sequence selected from of the α and β chain according to SEQ ID NO: 5 and 11 respectively, or 17 and 23 respectively; or 29 and 35 respectively.

The TCR α or γ chain of the invention may further comprise a CDR1 having at least 50%, 60%, 70%, 80%, 90%, 95%, 98%, 99%, or 100% sequence identity to an amino acid sequence selected from SEQ ID Nos. 1, 13, and 25; and/or a CDR2 having at least 50%, 60%, 70%, 80%, 90%, 95%, 98%, 99%, or 100% sequence identity to an amino acid sequence selected from SEQ ID Nos. 2, 14, and 26.

According to the invention the TCR β or δ chain may further comprise a CDR1 having at least 50%, 60%, 70%, 80%, 90%, 95%, 98%, 99%, or 100% sequence identity to an amino acid sequence selected from SEQ ID Nos. 7, 19, and 31; and/or a CDR2 having at least 50%, 60%, 70%, 80%, 90%, 95%, 98%, 99%, or 100% sequence identity to an amino acid sequence selected from SEQ ID Nos. 8, 20, and 32.

The antigen recognizing construct may in a further embodiment comprise a binding fragment of a TCR, and wherein said binding fragment comprises CDR1 to CDR3, optionally selected from the CDR1 to CDR3 sequences having the amino acid sequences of SEQ ID Nos. 1, 2, 3, or 7, 8, 9 or 13, 14, 15, or 19, 20, 21, or 25, 26, 27 or 31, 32, 33.

In further embodiments of the invention the antigen recognizing construct as described herein before is a TCR, or a fragment thereof, composed of at least one TCR α and one TCR β chain sequence, wherein said TCR α chain sequence comprises the CDR1 to CDR3 sequences having the amino acid sequences of SEQ ID NO: 1 to 3, and said TCR β chain sequence comprises the CDR1 to CDR3 sequences having the amino acid sequences of SEQ ID NO: 7 to 9; or wherein said TCR α chain sequence comprises the CDR1 to CDR3 sequences having the amino acid sequences of SEQ ID NO: 13 to 15, and said TCR β chain sequence comprises the CDR1 to CDR3 sequences having the amino acid sequences of SEQ ID NO: 19 to 21; or wherein said TCR α chain sequence comprises the CDR1 to CDR3 sequences having the amino acid sequences of SEQ ID NO: 25 to 27, and said TCR β chain sequence comprises the CDR1 to CDR3 sequences having the amino acid sequences of SEQ ID NO: 31 to 33.

In further embodiments of the invention the antigen recognizing construct as described herein before is a TCR, or a fragment thereof, comprising at least one TCR α and one TCR β chain sequence, wherein said TCR α chain sequence comprises a variable region sequence having the amino acid sequence of SEQ ID No. 4, and wherein said TCR β chain sequence comprises a variable region sequence having the amino acid sequence of SEQ ID No. 10; or wherein said TCR α chain sequence comprises a variable region sequence having the amino acid sequence of SEQ ID No. 16, and wherein said TCR β chain sequence comprises a variable region sequence having the amino acid sequence of SEQ ID No. 22; or wherein said TCR α chain sequence comprises a variable region sequence having the amino acid sequence of SEQ ID No. 28, and wherein said TCR β chain sequence comprises a variable region sequence having the amino acid sequence of SEQ ID No. 34.

In further embodiments of the invention the antigen recognizing construct as described herein before is a TCR, or a fragment thereof, further comprising a TCR constant region having at least 50%, 60%, 70%, 80%, 90%, 95%, 98%, 99%, or 100% sequence identity to an amino acid sequence selected from SEQ ID Nos. 5, 11, 17, 23, 29 and 35, preferably wherein the TCR is composed of at least one TCR α and one TCR β chain sequence, wherein the TCR α chain sequence comprises a constant region having at least 50%, 60%, 70%, 80%, 90%, 95%, 98%, 99%, or 100% sequence identity to an amino acid sequence selected from SEQ ID Nos. 5, 17, and 29.

Also disclosed are antigen recognizing constructs as described herein before comprising a first TCR chain having at least 50%, 60%, 70%, 80%, 90%, 95%, 98%, 99%, or 100% sequence identity to the amino acid sequence of SEQ ID No. 6, and a second TCR chain having at least 50%, 60%, 70%, 80%, 90%, 95%, 98%, 99%, or 100% sequence identity to the amino acid sequence of SEQ ID No. 12. The invention also provides TCRs comprising a first TCR chain having at least 50%, 60%, 70%, 80%, 90%, 95%, 98%, 99%, or 100% sequence identity to the amino acid sequence of SEQ ID No. 18, and a second TCR chain having at least 50%, 60%, 70%, 80%, 90%, 95%, 98%, 99%, or 100% sequence identity to the amino acid sequence of SEQ ID No. 24. In further embodiments the invention provides antigen recognizing constructs which are TCR and comprise a first TCR chain having at least 50%, 60%, 70%, 80%, 90%, 95%, 98%, 99%, or 100% sequence identity to the amino acid sequence of SEQ ID No. 30, and a second TCR chain having at least 50%, 60%, 70%, 80%, 90%, 95%, 98%, 99%, or 100% sequence identity to the amino acid sequence of SEQ ID No. 36.

As used herein, the term "murine" or "human," when referring to an antigen recognizing construct, or a TCR, or any component of a TCR described herein (e.g., complementarity determining region (CDR), variable region, constant region, α chain, and/or β chain), means a TCR (or component thereof), which is derived from a mouse or a human unrearranged TCR locus, respectively.

In an embodiment of the invention, chimeric TCR are provided, wherein the TCR chains comprise sequences from multiple species. Preferably, a TCR of the invention may comprise an α chain comprising a human variable region of an α chain and, for example, a murine constant region of a murine TCR α chain.

In one embodiment, the TCR of the invention is a human TCR comprising human variable regions according to the above embodiments and human constant regions.

The TCR of the invention may be provided as a single chain TCR (scTCR). A scTCR can comprise a polypeptide of a variable region of a first TCR chain (e.g., an alpha chain) and a polypeptide of an entire (full-length) second TCR chain (e.g., a beta chain), or vice versa. Furthermore, the scTCR can optionally comprise one or more linkers which join the two or more polypeptides together. The linker can be, for instance, a peptide, which joins together two single chains, as described herein. Also provided is such a scTCR of the invention, which is fused to a human cytokine, such as IL-2, IL-7 or IL-15.

The antigen recognizing construct according to the invention can also be provided in the form of a multimeric complex, comprising at least two scTCR molecules, wherein said scTCR molecules are each fused to at least one biotin moiety, and wherein said scTCRs are interconnected by biotin-streptavidin interaction to allow the formation of said multimeric complex. Similar approaches for the generation of multimeric TCR are also possible and included in this disclosure. Also provided are multimeric complexes of a higher order, comprising more than two scTCR of the invention.

For the purposes of the present invention, a TCR is a moiety having at least one TCR alpha or gamma and/or TCR beta or delta variable domain. Generally, they comprise both a TCR alpha variable domain and a TCR beta variable domain. They may be αβ heterodimers or may be in single chain format. For use in adoptive therapy, an αβ heterodimeric TCR may, for example, be transfected as full length chains having both cytoplasmic and transmembrane domains. If desired, an introduced disulfide bond between residues of the respective constant domains may be present.

In a preferred embodiment, the antigen recognizing construct is a human TCR, or fragment or derivative thereof. A human TCR or fragment or derivative thereof is a TCR, which comprises over 50% of the corresponding human TCR sequence. Preferably, only a small part of the TCR sequence is of artificial origin or derived from other species. It is known, however, that chimeric TCRs, e.g. derived from human origin with murine sequences in the constant domains, are advantageous. Particularly preferred are, therefore, TCRs in accordance with the present invention, which contains murine sequences in the extracellular part of their constant domains.

Thus, it is also preferred that the inventive antigen recognizing construct is able to recognize its antigen in a human leucocyte antigen (HLA) dependent manner, preferably in a HLA-A02 dependent manner. The term "HLA dependent manner" in the context of the present invention means that the antigen recognizing construct binds to the antigen only in the event that the antigenic peptide is presented by said HLA.

The antigen recognizing construct in accordance with the invention in one embodiment preferably induces an immune response, preferably wherein the immune response is characterized by the increase in interferon (IFN) γ levels.

Also provided by the invention is a polypeptide comprising a functional portion of any of the TCRs (or functional variants thereof) described herein, for examples, of any one of the TCRs selected from R4P1D10, R4P3F9, and R4P3H3, as provided in the example section and table 1. The term "polypeptide" as used herein includes oligopeptides and refers to a single chain of amino acids connected by one or more peptide bonds. With respect to the inventive polypeptides, the functional portion can be any portion comprising contiguous amino acids of the TCR (or functional variant thereof), of which it is a part, provided that the functional portion specifically binds to a COL6A3 antigen, preferably as disclosed herein in table 2, and peptides A1 to A9 (SEQ ID NOs: 59-67). The term "functional portion" when used in reference to a TCR (or functional variant thereof) refers to any part or fragment of the TCR (or functional variant thereof) of the invention, which part or fragment retains the biological activity of the TCR (or functional variant thereof), of which it is a part (the parent TCR or parent functional variant thereof). Functional portions encompass, for example, those parts of a TCR (or functional variant thereof) that retain the ability to specifically bind to a COL6A3 antigen (in an HLA-A2-dependent manner), or detect, treat, or prevent cancer, to a similar extent, the same extent, or to a higher extent, as the parent TCR (or functional variant thereof). In reference to the parent TCR (or functional variant thereof), the functional portion can comprise, for instance, about 10%, 25%, 30%, 50%, 68%, 80%, 90%, 95%, or more, of the parent TCR variable sequences (or functional variant thereof).

The functional portion can comprise additional amino acids at the amino or carboxy terminus of the portion, or at both termini, in which additional amino acids are not found in the amino acid sequence of the parent TCR or functional variant thereof. Desirably, the additional amino acids do not interfere with the biological function of the functional portion, e.g., specifically binding to COL6A3 antigens; and/or having the ability to detect cancer, treat or prevent cancer, etc. More desirably, the additional amino acids enhance the biological activity, as compared to the biological activity of the parent TCR or functional variant thereof.

The polypeptide can comprise a functional portion of either or both of the α and β chains of the TCRs or functional variant thereof of the invention, such as a functional portion comprising one of more of CDR1, CDR2, and (preferably) CDR3 of the variable region(s) of the α chain and/or β chain of a TCR or functional variant thereof of the invention. In an embodiment of the invention, the polypeptide can comprise a functional portion comprising the amino acid sequence of SEQ ID NO: 3, 9, 15, 21, 27, and 33 (CDR3 of the variable regions of the TCR of the invention), or a combination thereof. In an embodiment of the invention, the inventive polypeptide can comprise, for instance, the variable region of the inventive TCR or functional variant thereof comprising a combination of the CDR regions set forth above. In this regard, the polypeptide can comprise the amino acid sequence of any of SEQ ID NO: 4, 10, 16, 22, 28, and 34 (the variable regions of an α or β chain of the TCR of the invention).

In some instances, the construct of the invention may comprise one or two polypeptide chains comprising a sequences according to any of the SEQ ID NO: 1 to 36 (CDR sequences, constant and variable regions and full length sequences), or functional fragments thereof, and further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide may include any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods. In some embodiments of the invention, the TCRs (and functional portions and functional variants thereof), polypeptides, and proteins of the invention may be expressed as a single protein comprising a linker peptide linking the α chain and the β chain, and linking the γ chain and the δ chain. In this regard, the TCRs (and functional variants and functional portions thereof), polypeptides, and proteins of the invention comprising the amino acid sequences of the variable regions of the TCR of the invention and may further comprise a linker peptide. The linker peptide may advantageously facilitate the expression of a recombinant TCR (including functional portions and functional variants thereof), polypeptide, and/or protein in a host cell. The linker peptide may comprise any suitable amino acid sequence. Linker sequences for single chain TCR constructs are well known in the art. Such a single chain construct may further comprise one, or two, constant domain sequences. Upon expression of the construct including the linker peptide by a host cell, the linker peptide may also be cleaved, resulting in separated α and β chains, and separated γ and δ chain.

As already mentioned above, the binding functionality of the TCR of the invention may be provided in the framework of an antibody. The term "antibody" in its various grammatical forms is used herein to refer to immunoglobulin molecules and immunologically active portions of immunoglobulin molecules, i.e., molecules that contain an antigen-binding site or a paratope. Such molecules are also referred to as "antigen binding fragments" of immunoglobulin molecules. The invention further provides an antibody, or antigen binding portion thereof, which specifically binds to the antigens described herein. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form.

The invention also provides antigen binding portions of any of the antibodies described herein. The antigen binding portion can be any portion that has at least one antigen binding site, such as Fab, F(ab')2, dsFv, sFv, diabodies, and triabodies. A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques. Similarly, disulfide-stabilized variable region fragments (dsFv) can be prepared by recombinant DNA technology, antibody fragments of the invention, however, are not limited to these exemplary types of antibody fragments. Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles). In some instances, the TCR CDR3 sequence may be slightly modified, but preferably by not more than 3 amino acid residues, preferably only two and most preferably only one amino acid position, as compared to the CDR3 sequences provided in SEQ ID Nos: 3, 9, 15, 21, 27, and 33. Preferably, the antibodies comprise the CDR3, preferably all of CDR1 to CDR3 regions in the combination, as indicated for the TCR of the invention in table 1.

Suitable methods of making antibodies are known in the art. For instance, standard hybridoma methods are described in, e.g., Kohler and Milstein, Eur J Immunol, 5, 51 1-519 (1976), Harlow and Lane (eds.), Antibodies: A Laboratory Manual, CSH Press (1988), and C. A. Janeway et al. (eds.), Immunobiology, 8 Ed., Garland Publishing, New York, N.Y. (2011)). Alternatively, other methods, such as EBV-hybridoma methods (Haskard and Archer, J. Immunol. Methods, 74(2), 361-67 (1984), and Roder et al, Methods Enzymol, 121, 140-67 (1986)), and bacteriophage vector expression systems (see, e.g., Huse et al., Science, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266.

Some embodiments of the invention also pertain to TCRs, or functional fragments and polypeptides thereof, which are soluble TCRs. As used herein, the term "soluble T-cell receptor" refers to heterodimeric truncated variants of native TCRs, which comprise extracellular portions of the TCR α-chain and β-chain linked by a disulfide bond, but which lack the transmembrane and cytosolic domains of the native protein. The terms "soluble T-cell receptor α-chain sequence and soluble T-cell receptor β-chain sequence" refer to TCR α-chain and β-chain sequences that lack the transmembrane and cytosolic domains. The sequence (amino acid or nucleic acid) of the soluble TCR α-chain and β-chains may be identical to the corresponding sequences in a native TCR or may comprise variant soluble TCR α-chain and β-chain sequences, as compared to the corresponding native TCR sequences. The term "soluble T-cell receptor" as used herein encompasses soluble TCRs with variant or non-variant soluble TCR α-chain and β-chain sequences. The variations may be in the variable or constant regions of the soluble TCR α-chain and β-chain sequences and can include, but are not limited to, amino acid deletion, insertion, substitution mutations as well as changes to the nucleic acid sequence, which do not alter the amino acid sequence. Soluble TCR of the invention in any case retain the binding functionality of their parent molecules.

The above problem is further solved by a nucleic acid encoding for an antigen recognizing construct of the invention, or any of the aforementioned protein or polypeptide constructs. The nucleic acid preferably (a) has a strand encoding for an antigen recognizing construct according to the invention; (b) has a strand complementary to the strand in (a); or (c) has a strand that hybridizes under stringent conditions with a molecule as described in (a) or (b). Stringent conditions are known to the person of skill in the art, specifically from Sambrook et al, "Molecular Cloning". In addition to that, the nucleic acid optionally has further sequences, which are necessary for expressing the nucleic acid sequence corresponding to the protein, specifically for expression in a mammalian/human cell. The nucleic acid used can be contained in a vector suitable for allowing expression of the nucleic acid sequence corresponding to the peptide in a cell. However, the nucleic acids can also be used to transform an antigen-presenting cell, which may not be restricted to classical antigen-presenting cells, such as dendritic cells, in such a way that they themselves produce the corresponding proteins on their cellular surface.

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and can contain a natural, non-natural or altered internucleotide linkage, such as a phosphoroamidate linkage or a phosphorothioate linkage, instead of the phosphodiester found between the nucleotides of an unmodified oligonucleotide.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication. The nucleic acid can comprise any nucleotide sequence, which encodes any of the TCRs, polypeptides, or proteins, or functional portions or functional variants thereof described herein.

Furthermore, the invention provides a vector comprising a nucleic acid in accordance to the invention as described above. Desirably, the vector is an expression vector or a recombinant expression vector. The term "recombinant expression vector" refers in context of the present invention to a nucleic acid construct that allows for the expression of an mRNA, protein or polypeptide in a suitable host cell. The recombinant expression vector of the invention can be any suitable recombinant expression vector, and can be used to transform or transfect any suitable host. Suitable vectors include those designed for propagation and expansion or for expression or both, such as plasmids and viruses. Examples of animal expression vectors include pEUK-Cl, pMAM, and pMAMneo. Preferably, the recombinant expression vector is a viral vector, e.g., a retroviral vector. The recombinant expression vector comprises regulatory sequences, such as transcription and translation initiation and termination codons, which are specific to the type of host cell (e.g., bacterium, fungus, plant, or animal), into which the vector is to be introduced and in which the expression of the nucleic acid of the invention may be performed. Furthermore, the vector of the invention may include one or more marker genes, which allow for selection of transformed or transfected hosts. The recombinant expression vector can comprise a native or normative promoter operably linked to the nucleotide sequence encoding the constructs of the invention, or to the nucleotide sequence, which is complementary to or which hybridizes to the nucleotide sequence encoding the constructs of the invention. The selections of promoters include, e.g., strong, weak, inducible, tissue-specific and developmental-specific promoters. The promoter can be a non-viral promoter or a viral promoter. The inventive recombinant expression vectors can be designed for either transient expression, for stable expression, or for both. Also, the recombinant expression vectors can be made for constitutive expression or for inducible expression.

The invention also pertains to a host cell comprising an antigen recognizing construct in accordance with the invention. Specifically, the host cell of the invention comprises a nucleic acid, or a vector as described herein above. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood leukocyte (PBL) or a peripheral blood mononuclear cell (PBMC). More preferably, the host cell is a T cell. The T cell can be any T cell, such as a cultured T cell, e.g., a primary T cell, or a T cell from a cultured T cell line, e.g., Jurkat, SupT1, etc., or a T cell obtained from a mammal, preferably a T cell or T cell precursor from a human patient. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. More preferably, the T cell is a T cell isolated from a human. The T cell can be any type of T cell and can be of any developmental stage, including but not limited to, CD4-positive and/or CD8-positive, CD4-positive helper T cells, e.g., Th1 and Th2 cells, CD8-positive T cells (e.g., cyto-toxic T cells), tumor infiltrating cells (TILs), memory T cells, naive T cells, and the like. Preferably, the T cell is a CD8-positive T cell or a CD4-positive T cell.

Preferably, the host cell of the invention is a lymphocyte, preferably, a T lymphocyte, such as a CD4-positive or CD8-positive T-cell. The host cell furthermore preferably is a tumor reactive T cell specific for COL6A3 expressing tumor cells.

One further aspect of the present invention relates to the herein disclosed antigen recognizing constructs, nucleic acids, vectors, pharmaceutical compositions and/or host cell for use in medicine. The use in medicine in one preferred embodiment includes the use in the diagnosis, prevention and/or treatment of a tumor disease, such as a malignant or benign tumor disease. The tumor disease is, for example, a tumor disease characterized by the expression of COL6A3, in a cancer or tumor cell of said tumor disease.

With respect to the above mentioned medical applications of the antigen recognizing constructs and other materials derived therefrom, the to be treated and/or diagnosed cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, esophageal cancer, cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is cancer is cancer of the uterine cervix, oropharynx, anus, anal canal, anorectum, vagina, vulva, or penis. A particularly preferred cancer is a COL6A3 positive cancer, including gastrointestinal and gastric cancer.

The constructs, proteins, TCRs antibodies, polypeptides and nucleic acids of the invention are in particular for use in immune therapy, preferably, in adoptive T cell therapy. The administration of the compounds of the invention can, for example, involve the infusion of T cells of the invention into said patient. Preferably, such T cells are autologous T cells of the patient and in vitro transduced with a nucleic acid or antigen recognizing construct of the present invention.

WO 2016/011210 discloses engineered cells for adoptive therapy, including NK cells and T cells, and compositions containing the cells, and methods for their administration to subjects.

The cells can contain genetically engineered antigen receptors that specifically bind to antigens, such as chimeric antigen receptors (CARs) and costimulatory receptors.

The objective of the invention is also solved by a method of manufacturing a COL6A3 specific antigen recognizing construct expressing cell line, comprising
 a. Providing a suitable host cell,
 b. Providing a genetic construct comprising a coding sequence encoding for an antigen recognizing construct according to the herein disclosed invention,
 c. Introducing into said suitable host cell said genetic construct, and
 d. Expressing said genetic construct by said suitable host cell.

The method may further comprise a step of cell surface presentation of said antigen recognizing construct on said suitable host cell.

In other preferred embodiments, the genetic construct is an expression construct comprising a promoter sequence operably linked to said coding sequence.

Preferably, said antigen recognizing construct is of mammalian origin, preferably of human origin. The preferred suitable host cell for use in the method of the invention is a mammalian cell, such as a human cell, in particular a human T lymphocyte. T cells for use in the invention are described in detail herein above.

Also encompassed by the invention are embodiments, wherein said antigen recognizing construct is a modified TCR, wherein said modification is the addition of functional domains, such as a label or a therapeutically active substance. Furthermore, encompassed are TCR having alternative domains, such as an alternative membrane anchor domain instead of the endogenous transmembrane region.

Desirably, the transfection system for introducing the genetic construct into said suitable host cell is a retroviral vector system. Such systems are well known to the skilled artisan.

Also comprised by the present invention is in one embodiment the additional method step of isolation and purification of the antigen recognizing construct from the cell and, optionally, the reconstitution of the translated antigen recognizing construct-fragments in a T-cell.

In an alternative aspect of the invention a T-cell is provided obtained or obtainable by a method for the production of a T cell receptor (TCR), which is specific for tumorous cells and has high avidity as described herein above. Such a T cell is depending on the host cell used in the method of the invention, for example, a human or non-human T-cell, preferably a human TCR.

The inventive TCRs, polypeptides, proteins, (including functional variants thereof), nucleic acids, recombinant expression vectors, host cells (including populations thereof), and antibodies (including antigen binding portions thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% o, 80%, 90%, 95%, or can be 100%.

The inventive antigen recognizing constructs, TCRs, polypeptides, proteins (including functional variants thereof), nucleic acids, recombinant expression vectors, host cells (including populations thereof), and antibodies (including antigen binding portions thereof), all of which are collectively referred to as "inventive TCR materials" hereinafter, can be formulated into a composition, such as a pharmaceutical composition. In this regard, the invention provides a pharmaceutical composition comprising any of the antigen recognizing constructs, TCRs, polypeptides, proteins, functional portions, functional variants, nucleic acids, expression vectors, host cells (including populations thereof), and antibodies (including antigen binding portions thereof) described herein, and a pharmaceutically acceptable carrier, excipient and/or stabilizer. The inventive pharmaceutical compositions containing any of the inventive TCR materials can comprise more than one inventive TCR material, e.g., a polypeptide and a nucleic acid, or two or more different TCRs (including functional portions and functional variants thereof). Alternatively, the pharmaceutical composition can comprise an inventive TCR material in combination with another pharmaceutically active agent(s) or drug(s), such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. Preferably, the carrier is a pharmaceutically acceptable carrier. With respect to pharmaceutical compositions, the carrier can be any of those conventionally used for the particular inventive TCR material under consideration. Such pharmaceutically acceptable carriers are well-known to those skilled in the art and are readily available to the public. It is preferred that the pharmaceutically acceptable carrier be one, which has no detrimental side effects or toxicity under the conditions of use.

Thus also provided is a pharmaceutical composition, comprising any of the herein described products of the invention and TCR materials of the invention, specifically any proteins, nucleic acids or host cells. In a preferred embodiment the pharmaceutical composition is for immune therapy, preferably adoptive cell therapy.

Preferably, the inventive TCR material is administered by injection, e.g., intravenously. When the inventive TCR material is a host cell expressing the inventive TCR (or functional variant thereof), the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumen.

For purposes of the invention, the amount or dose (e.g., numbers of cells when the inventive TCR material is one or more cells) of the inventive TCR material administered may be sufficient to affect, e.g., a therapeutic or prophylactic response, in the subject or animal over a reasonable time frame. For example, the dose of the inventive TCR material should be sufficient to bind to a cancer antigen, or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

It is contemplated that the inventive pharmaceutical compositions, TCRs (including functional variants thereof), polypeptides, proteins, nucleic acids, recombinant expression vectors, host cells, or populations of cells can be used in methods of treating or preventing cancer, or COL6A3-positive premalignancy. The inventive TCRs (and functional variants thereof) are believed to bind specifically to COL6A3 antigen, such that the TCR (or related inventive polypeptide or protein and functional variants thereof), when expressed by a cell, is able to mediate an immune response against a target cell expressing the COL6A3 antigens of the invention. In this regard, the invention provides a method of treating or preventing a condition, in particular cancer, in a mammal, comprising administering to the mammal any of the pharmaceutical compositions, antigen recognizing constructs, in particular TCRs (and functional variants thereof), polypeptides, or proteins described herein, any nucleic acid or recombinant expression vector comprising a nucleotide sequence encoding any of the TCRs (and functional variants thereof), polypeptides, proteins described herein, or any host cell or population of cells comprising a recombinant vector, which encodes any of the constructs of the invention (and functional variants thereof), polypeptides, or proteins described herein, in an amount effective to treat or prevent the condition in the mammal, wherein the condition is cancer, preferably COL6A3 positive cancer.

Examples of pharmaceutically acceptable carriers or diluents useful in the present invention include stabilizers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of a condition in a mammal. Furthermore, the treatment or prevention provided by the inventive method can include treatment or prevention of one or more conditions or symptoms of the condition, e.g., cancer, being treated or prevented. For example, treatment or prevention can include promoting the regression of a tumor. Also, for purposes herein, "prevention" can encompass delaying the onset of the condition, or a symptom or condition thereof.

The present invention also relates to a method of treating cancer comprising administering a TCR, a nucleic acid, or a host cell of the present description in combination with at least one chemotherapeutic agent and/or radiation therapy.

Also provided is a method of treating cancer in a subject in need thereof, comprising:
  a) isolating a cell from said subject;
  b) transforming the cell with at least one vector encoding an antigen recognizing construct of the present invention to produce a transformed cell;
  c) expanding the transformed cell to produce a plurality of transformed cells; and
  d) administering the plurality of transformed cells to said subject.

Also provided is a method of treating cancer in a subject in need thereof, comprising:
  a) isolating a cell from a healthy donor;
  b) transforming the cell with a vector encoding an antigen recognizing construct of the present invention to produce a transformed cell;
  c) expanding the transformed cell to produce a plurality of transformed cells; and
  d) administering the plurality of transformed cells to said subject.

Also provided is a method of detecting cancer in a biological sample comprising:
  a) contacting the biological sample with an antigen recognizing construct of the present description;

b) detecting binding of the antigen recognizing construct to the biological sample.

In some embodiments, the method of detecting cancer is carried out in vitro, in vivo or in situ.

Also provided is a method of detecting the presence of a condition in a mammal. The method comprises (i) contacting a sample comprising one or more cells from the mammal with any of the inventive TCRs (and functional variants thereof), polypeptides, proteins, nucleic acids, recombinant expression vectors, host cells, populations of cells, antibodies, or antigen binding portions thereof, or pharmaceutical compositions described herein, thereby forming a complex, and detecting the complex, wherein detection of the complex is indicative of the presence of the condition in the mammal, wherein the condition is cancer, such as a COL6A3-positive malignancy.

With respect to the inventive method of detecting a condition in a mammal, the sample of cells can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting can take place in vitro or in vivo with respect to the mammal. Preferably, the contacting is in vitro.

Also, detection of the complex can occur through any number of ways known in the art. For instance, the inventive antigen recognizing constructs (and functional variants thereof), polypeptides, proteins, nucleic acids, recombinant expression vectors, host cells, populations of cells, or antibodies or TCRs, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the above mentioned medical applications of the TCR material of the invention, the to be treated and/or diagnosed cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, esophageal cancer, cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is cancer is cancer of the uterine cervix, oropharynx, anus, anal canal, anorectum, vagina, vulva, or penis. A particularly preferred cancer is a COL6A3 positive cancer, such as gastrointestinal or gastric cancer.

In general, the invention provides a method for treating a subject suffering from a tumor or tumor disease comprising the administration of the antigen recognizing constructs, nucleic acids, vectors, pharmaceutical compositions and/or host cell as disclosed by the present invention.

Preferably the subject is a subject in need of such a treatment. The subject in preferred embodiments is a mammalian subject, preferably a human patient, suffering from a tumor or tumor disease, which is COL6A3-positive.

BRIEF DESCRIPTION OF DRAWINGS

The patent or application file contains at least one drawing executed in color. Copies of this patent or patent application publication with color drawing(s) will be provided by the Office upon request and payment of the necessary fee.

The present invention will now be further described in the following examples with reference to the accompanying figures and sequences, nevertheless, without being limited thereto. For the purposes of the present invention, all references as cited herein are incorporated by reference in their entireties. In the Figures and Sequences:

FIG. 12: HLA-A*02/COL6A3-002 tetramer and HLA-A*02/NYESO1-001 tetramer staining, respectively, of SUP-T1 cells electroporated with alpha and beta chain RNA of TCR R4P3H3 or NYESO1-001-specific control TCR 1G4 (Table 1). Mock electroporated SUP-T1 cells serve as control.

DETAILED DESCRIPTION OF THE INVENTION

TABLE 1

TCR sequences of the invention

Figure 1:
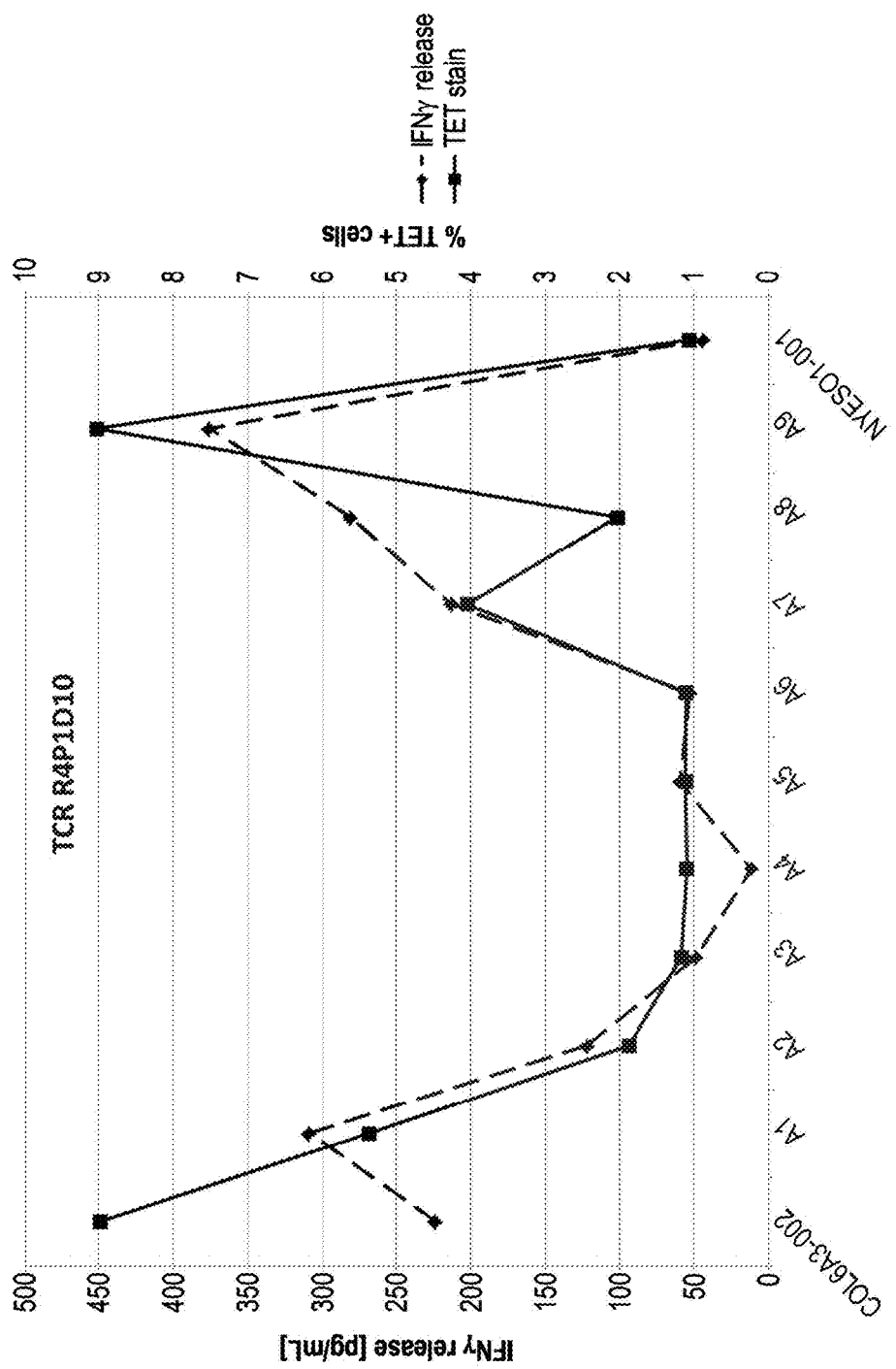
FIG. 1: IFNγ release (left axis) and HLA-A*02/COL6A3-002 tetramer staining (right axis) of human primary CD8+ T-cells of one donor electroporated with alpha and beta chain RNA of TCR R4P1D10 (Table 1), respectively, after co-incubation with K562-A2 target cells (see Hirano N. et al; Blood. 2006 Feb. 15; 107(4):1528-36) loaded with COL6A3-002 peptide (SEQ ID NO:58), various COL6A3-002 alanine or glycine substitution variants at positions 1-9 of (SEQ ID NO:59-67), or NYESO1-001 control peptide (SEQ ID NO:68).

| SEQ ID NO: | TCR | Chain | Region | Sequence |
|---|---|---|---|---|
| 1 | R4P1D10 | alpha | CDR1 | DRGSQS |
| 2 | R4P1D10 | alpha | CDR2 | IY |
| 3 | R4P1D10 | alpha | CDR3 | CAVNFHDKIIF |
| 4 | R4P1D10 | alpha | variable domain | MKSLRVLLVILWLQLSWVWSQQKEVEQNSGPLSVPEGAIASLNCTYSDRGSQSFFWYRQYSGKSPELIMFIYSNGDKEDGRFTAQLNKASQYVSLLIRDSQPSDSATYLCAVN |
| 5 | R4P1D10 | alpha | constant domain | NIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 6 | R4P1D10 | alpha | full-length | MKSLRVLLVILWLQLSWVWSQQKEVEQNSGPLSVPEGAIASLNCTYSDRGSQSFFWYRQYSGKSPELIMFIYSNGDKEDGRFTAQLNKASQYVSLLIRDSQPSDSATYLCAVNFHDKIIFGKGTRLHILPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 7 | R4P1D10 | beta | CDR1 | SGDLS |
| 8 | R4P1D10 | beta | CDR2 | YYNGEE |
| 9 | R4P1D10 | beta | CDR3 | CASSVASAYGYTF |
| 10 | R4P1D10 | beta | variable domain | MGFRLLCCVAFCLLGAGPVDSGVTQTPKHLITATGQRVTLRCSPRSGDLSVYWYQQSLDQGLQFLIHYYNGEERAKGNILERFSAQQFPDLHSELNLSSLELGDSALYFCASSV |

TABLE 1-continued

TCR sequences of the invention

| SEQ ID NO: | TCR | Chain | Region | Sequence |
|---|---|---|---|---|
| 11 | R4P1D10 | beta | constant domain | EDLNKVFPPEVAVFEPSEAEISHTQK ATLVCLATGFFPDHVELSWWVNGK EVHSGVSTDPQPLKEQPALNDSRYC LSSRLRVSATFWQNPRNHFRCQVQF YGLSENDEWTQDRAKPVTQIVSAEA WGRADCGFTSVSYQQGVLSATILYE ILLGKATLYAVLVSALVLMAMVKR KDF |
| 12 | R4P1D10 | beta | full-length | MGFRLLCCVAFCLLGAGPVDSGVTQ TPKHLITATGQRVTLRCSPRSGDLSV YWYQQSLDQGLQFLIHYYNGEERA KGNILERFSAQQFPDLHSELNLSSLE LGDSALYFCASSVASAYGYTFGSGT RLTVVEDLNKVFPPEVAVFEPSEAEI SHTQKATLVCLATGFFPDHVELSW WVNGKEVHSGVSTDPQPLKEQPAL NDSRYCLSSRLRVSATFWQNPRNHF RCQVQFYGLSENDEWTQDRAKPVT QIVSAEAWGRADCGFTSVSYQQGVL SATILYEILLGKATLYAVLVSALVLM AMVKRKDF |
| 13 | R4P3F9 | alpha | CDR1 | DRGSQS |
| 14 | R4P3F9 | alpha | CDR2 | IY |
| 15 | R4P3F9 | alpha | CDR3 | CAAYSGAGSYQLTF |
| 16 | R4P3F9 | alpha | variable domain | MKSLRVLLVILWLQLSWVWSQQKE VEQNSGPLSVPEGAIASLNCTYSDRG SQSFFWYRQYSGKSPELIMFIYSNGD KEDGRFTAQLNKASQYVSLLIRDSQ PSDSATYLCA |
| 17 | R4P3F9 | alpha | constant domain | NIQNPDPAVYQLRDSKSSDKSVCLFT DFDSQTNVSQSKDSDVYITDKTVLD MRSMDFKSNSAVAWSNKSDFACAN AFNNSIIPEDTFFPSPESSCDVKLVEK SFETDTNLNFQNLSVIGFRILLLKVA GFNLLMTLRLWSS |
| 18 | R4P3F9 | alpha | full-length | MKSLRVLLVILWLQLSWVWSQQKE VEQNSGPLSVPEGAIASLNCTYSDRG SQSFFWYRQYSGKSPELIMFIYSNGD KEDGRFTAQLNKASQYVSLLIRDSQ PSDSATYLCAAYSGAGSYQLTFGKG TKLSVIPNIQNPDPAVYQLRDSKSSD KSVCLFTDFDSQTNVSQSKDSDVYIT DKTVLDMRSMDFKSNSAVAWSNKS DFACANAFNNSIIPEDTFFPSPESSCD VKLVEKSFETDTNLNFQNLSVIGFRI LLLKVAGFNLLMTLRLWSS |
| 19 | R4P3F9 | beta | CDR1 | SGDLS |
| 20 | R4P3F9 | beta | CDR2 | YYNGEE |
| 21 | R4P3F9 | beta | CDR3 | CASSVESSYGYTF |
| 22 | R4P3F9 | beta | variable domain | MGFRLLCCVAFCLLGAGPVDSGVTQ TPKHLITATGQRVTLRCSPRSGDLSV YWYQQSLDQGLQFLIHYYNGEERA KGNILERFSAQQFPDLHSELNLSSLE LGDSALYFCASSV |

TABLE 1-continued

TCR sequences of the invention

| SEQ ID NO: | TCR | Chain | Region | Sequence |
|---|---|---|---|---|
| 23 | R4P3F9 | beta | constant domain | EDLNKVFPPEVAVFEPSEAEISHTQK ATLVCLATGFFPDHVELSWWVNGK EVHSGVSTDPQPLKEQPALNDSRYC LSSRLRVSATFWQNPRNHFRCQVQF YGLSENDEWTQDRAKPVTQIVSAEA WGRADCGFTSVSYQQGVLSATILYE ILLGKATLYAVLVSALVLMAMVKR KDF |
| 24 | R4P3F9 | beta | full-length | MGFRLLCCVAFCLLGAGPVDSGVTQ TPKHLITATGQRVTLRCSPRSGDLSV YWYQQSLDQGLQFLIQYYNGEERA KGNILERFSAQQFPDLHSELNLSSLE LGDSALYFCASSVESSYGYTFGSGTR LTVVEDLNKVFPPEVAVFEPSEAEIS HTQKATLVCLATGFFPDHVELSWW VNGKEVHSGVSTDPQPLKEQPALND SRYCLSSRLRVSATFWQNPRNHFRC QVQFYGLSENDEWTQDRAKPVTQIV SAEAWGRADCGFTSVSYQQGVLSA TILYEILLGKATLYAVLVSALVLMA MVKRKDF |
| 25 | R4P3H3 | alpha | CDR1 | DRGSQS |
| 26 | R4P3H3 | alpha | CDR2 | IY |
| 27 | R4P3H3 | alpha | CDR3 | CAVKAGNQFYF |
| 28 | R4P3H3 | alpha | variable domain | MKSLRVLLVILWLQLSWVWSQQKE VEQNSGPLSVPEGAIASLNCTYSDRG SQSFFWYRQYSGKSPELIMFIYSNGD KEDGRFTAQLNKASQYVSLLIRDSQ PSDSATYLCAV |
| 29 | R4P3H3 | alpha | constant domain | NIQNPDPAVYQLRDSKSSDKSVCLFT DFDSQTNVSQSKDSDVYITDKTVLD MRSMDFKSNSAVAWSNKSDFACAN AFNNSIIPEDTFFPSPESSCDVKLVEK SFETDTNLNFQNLSVIGFRILLLKVA GFNLLMTLRLWSS |
| 30 | R4P3H3 | alpha | full-length | MKSLRVLLVILWLQLSWVWSQQKE VEQNSGPLSVPEGAIASLNCTYSDRG SQSFFWYRQYSGKSPELIMFIYSNGD KEDGRFTAQLNKASQYVSLLIRDSQ PSDSATYLCAVKAGNQFYFGTGTSL TVIPNIQNPDPAVYQLRDSKSSDKSV CLFTDFDSQTNVSQSKDSDVYITDKT VLDMRSMDFKSNSAVAWSNKSDFA CANAFNNSIIPEDTFFPSPESSCDVKL VEKSFETDTNLNFQNLSVIGFRILLL KVAGFNLLMTLRLWSS |
| 31 | R4P3H3 | beta | CDR1 | SGHVS |
| 32 | R4P3H3 | beta | CDR2 | FQNEAQ |
| 33 | R4P3H3 | beta | CDR3 | CASSLLTSGGDNEQFF |
| 34 | R4P3H3 | beta | variable domain | MGTRLLCWVVLGFLGTDHTGAGVS QSPRYKVAKRGQDVALRCDPISGHV SLFWYQQALGQGPEFLTYFQNEAQL DKSGLPSDRFFAERPEGSVSTLKIQR TQQEDSAVYLCASSL |
| 35 | R4P3H3 | beta | constant domain | EDLKNVFPPEVAVFEPSEAEISHTQK ATLVCLATGFYPDHVELSWWVNGK EVHSGVSTDPQPLKEQPALNDSRYC LSSRLRVSATFWQNPRNHFRCQVQF YGLSENDEWTQDRAKPVTQIVSAEA WGRADCGFTSESYQQGVLSATILYEI LLGKATLYAVLVSALVLMAMVKRK DSRG |

TABLE 1-continued

TCR sequences of the invention

| SEQ ID NO: | TCR | Chain | Region | Sequence |
|---|---|---|---|---|
| 36 | R4P3H3 | beta | full-length | MGTRLLCWVVLGFLGTDHTGAGVS QSPRYKVAKRGQDVALRCDPISGHV SLFWYQQALGQGPEFLTYFQNEAQL DKSGLPSDRFFAERPEGSVSTLKIQR TQQEDSAVYLCASSLLTSGGDNEQF FGPGTRLTVLEDLKNVFPPEVAVFEP SEAEISHTQKATLVCLATGFYPDHVE LSWWVNGKEVHSGVSTDPQPLKEQ PALNDSRYCLSSRLRVSATFWQNPR NHFRCQVQFYGLSENDEWTQDRAK PVTQIVSAEAWGRADCGFTSESYQQ GVLSATILYEILLGKATLYAVLVSAL VLMAMVKRKDSRG |
| 37 | 1G4 | alpha | CDR1 | DSAIYN |
| 38 | 1G4 | alpha | CDR2 | IQS |
| 39 | 1G4 | alpha | CDR3 | CAVRPTSGGSYIPTF |
| 40 | 1G4 | alpha | variable domain | METLLGLLILWLQLQWVSSKQEVTQ IPAALSVPEGENLVLNCSFTDSAIYN LQWFRQDPGKGLTSLLLIQSSQREQT SGRLNASLDKSSGRSTLYIAASQPGD SATYLCAVR |
| 41 | 1G4 | alpha | constant domain | YIQNPDPAVYQLRDSKSSDKSVCLFT DFDSQTNVSQSKDSDVYITDKTVLD MRSMDFKSNSAVAWSNKSDFACAN AFNNSIIPEDTFFPSPESSCDVKLVEK SFETDTNLNFQNLSVIGFRILLLKVA GFNLLMTLRLWSS |
| 42 | 1G4 | alpha | full-length | METLLGLLILWLQLQWVSSKQEVTQ IPAALSVPEGENLVLNCSFTDSAIYN LQWFRQDPGKGLTSLLLIQSSQREQT SGRLNASLDKSSGRSTLYIAASQPGD SATYLCAVRPTSGGSYIPTFGRGTSLI VHPYIQNPDPAVYQLRDSKSSDKSV CLFTDFDSQTNVSQSKDSDVYITDKT VLDMRSMDFKSNSAVAWSNKSDFA CANAFNNSIIPEDTFFPSPESSCDVKL VEKSFETDTNLNFQNLSVIGFRILLL KVAGFNLLMTLRLWSS |
| 43 | 1G4 | beta | CDR1 | MNHEY |
| 44 | 1G4 | beta | CDR2 | SVGAGI |
| 45 | 1G4 | beta | CDR3 | CASSYVGNTGELFF |
| 46 | 1G4 | beta | variable domain | MSIGLLCCAALSLLWAGPVNAGVTQ TPKFQVLKTGQSMTLQCAQDMNHE YMSWYRQDPGMGLRLIHYSVGAGI TDQGEVPNGYNVSRSTTEDFPLRLLS AAPSQTSVYFCASSY |
| 47 | 1G4 | beta | constant domain | EDLKNVFPPEVAVFEPSEAEISHTQK ATLVCLATGFYPDHVELSWWVNGK EVHSGVSTDPQPLKEQPALNDSRYC LSSRLRVSATFWQNPRNHFRCQVQF YGLSENDEWTQDRAKPVTQIVSAEA WGRADCGFTSESYQQGVLSATILYEI LLGKATLYAVLVSALVLMAMVKRK DSRG |
| 48 | 1G4 | beta | full-length | MSIGLLCCAALSLLWAGPVNAGVTQ TPKFQVLKTGQSMTLQCAQDMNHE YMSWYRQDPGMGLRLIHYSVGAGI TDQGEVPNGYNVSRSTTEDFPLRLLS AAPSQTSVYFCASSYVGNTGELFFG EGSRLTVLEDLKNVFPPEVAVFEPSE AEISHTQKATLVCLATGFYPDHVELS |

TABLE 1-continued

TCR sequences of the invention

| SEQ ID NO: | TCR | Chain | Region | Sequence |
|---|---|---|---|---|
| | | | | WWVNGKEVHSGVSTDPQPLKEQPA LNDSRYCLSSRLRVSATFWQNPRNH FRCQVQFYGLSENDEWTQDRAKPV TQIVSAEAWGRADCGFTSESYQQGV LSATILYEILLGKATLYAVLVSALVL MAMVKRKDSRG |

TABLE 2

Peptide sequences of the invention

| Peptide Code | Sequence | SEQ ID NO: |
|---|---|---|
| AGRN-001 | ALLDGRVQL | 49 |
| CLASP1-001 | RLLDGAFKL | 50 |
| COL6A1-001 | ILLDGSASV | 51 |
| COL6A2-001 | FLLDGSERL | 52 |
| COL6A3-006 | FLFDGSANLV | 53 |
| COL6A3-008 | FLFDGSANL | 54 |
| COL6A3-014 | FLLDGSEGV | 55 |
| VWA2-001 | FLLDGSNSV | 56 |
| VWF-001 | FLLDGSSRL | 57 |
| COL6A3-002 | FLLDGSANV | 58 |
| A1 | ALLDGSANV | 59 |
| A2 | FALDGSANV | 60 |
| A3 | FLADGSANV | 61 |
| A4 | FLLAGSANV | 62 |
| A5 | FLLDASANV | 63 |
| A6 | FLLDGAANV | 64 |
| A7 | FLLDGSGNV | 65 |
| A8 | FLLDGSAAV | 66 |
| A9 | FLLDGSANA | 67 |
| NYES01-001 | SLLMWITQV | 68 |

EXAMPLES

In an aspect, allo-reactive settings are used to circumvent self-tolerance and yield T-cells with a higher avidity when compared to T-cells derived from autologous settings, i.e., patients. Examples of such settings include in vitro generation of allo-HLA reactive, peptide-specific T-cells (Sadovnikova et al. 1998; Savage et al. 2004; Wilde et al. 2012), and immunization of mice transgenic for human-MHC or human TCR (Stanislawski et al. 2001; Li et al. 2010), each of which are incorporated by reference in their entireties.

To isolate high avidity T-cells from allo-reactive setting, PBMCs from HLA-A*02-negative healthy donors are used after obtaining informed consent. Recombinant biotinylated HLA-A*02 class I monomers and A2 fluorescent tetramers containing COL6A3-002 are obtained from MBLI (Woburn, Mass.). PBMCs are incubated with anti-CD20SA diluted in phosphate buffered saline (PBS) for 1 hour at room temperature, washed, and incubated with the biotinylated HLA-A*02/COL6A3-002 monomers for 30 minutes at room temperature, washed, and plated at $3 \times 10^6$ cells/well in 24-well plates in RPMI with 10% human AB serum. Interleukin 7 (IL-7; R&D Systems, Minneapolis, Minn.) was added on day 1 at 10 ng/mL and IL-2 (Chiron, Harefield, United Kingdom) was added at 10 U/mL on day 4. Over a 5-week period cells were restimulated weekly with fresh PBMCs, mixed with responder cells at a 1:1 ratio, and plated at $3 \times 10^6$/well in 24-well plates.

To obtain high avidity T-cells, approximately $10^6$ PBMCs with HLA-A*02/COL6A3-002 tetramer-phycoerythrin (PE) (obtained from MBLI) were incubated for 30 minutes at 37° C., followed by anti-CD8-fluorescein isothiocyanate (FITC)/allophycocyanin (APC) for 20 minutes at 4° C., followed by fluorescence activated cell sorting. Sorted tetramer-positive cells were expanded in 24-well plates using, per well, $2 \times 10^5$ sorted cells, $2 \times 10^6$ irradiated A2-negative PBMCs as feeders, $2 \times 10^4$ CD3/CD28 beads/mL (Dynal, Oslo Norway), and IL-2 (1000 U/mL). The high avidity T-cells, thus obtained, were then used to identify and isolate TCRs using techniques known in the art, such as single cell 5' RACE (Rapid Amplification of cDNA Ends). Non-redundant TCR DNAs were then analyzed for amino acid/DNA sequences determination and cloning into expression vectors.

Three COL6A3-002-specific TCRs (R4P1D10, R4P3F9 and R4P3H3, see Table 2), each encoding tumor specific TCR-alpha and TCR-beta chains, were isolated and amplified from T-cells of healthy donors. Cells from healthy donors were in vitro stimulated according to a method previously described (Walter et al., 2003 J Immunol., Nov. 15; 171(10):4974-8). COL6A3 peptide presentation was performed as described previously (Hirano N. et al; Blood. 2006 Feb. 15; 107(4):1528-36). Target-specific cells were single-cell sorted using HLA-A*02 multimers and then used for subsequent TCR isolation. TCR sequences were isolated via 5' RACE by standard methods as described by e.g. Molecular Cloning a laboratory manual fourth edition by Green and Sambrook. The alpha and beta variable regions of TCRs R4P1D10, R4P3F9 and R4P3H3 were sequenced and cloned for further functional characterization. R4P1D10 and R4P3H3 are derived from HLA-A*02 positive donors and R4P3F9 is derived from a HLA-A*02 negative donor (allo-reactive setting).

TABLE 3

SPR affinity of COL6A3-002 and NYESO1-001 TCRs

| TCR | Equilibrium dissociation constant ($K_D$) for HLA-A02/COL6A3-002 complex in µM | Equilibrium dissociation constant ($K_D$) for HLA-A02/NYESO1-001 complex in µM |
| --- | --- | --- |
| R4P1D10 | 16 | no binding |
| R4P3F9 | 62 | no binding |
| R4P3H3 | 102 | no binding |
| 1G4 | no binding | 7 |

Example 1: T-Cell Receptor R4P1D10

The TCR R4P1D10 alpha and beta chains were cloned as described previously, for example, as described in U.S. Pat. No. 8,519,100, the content of which is hereby incorporated by reference in its entirety for said methods. TCR R4P1D10 is restricted towards HLA-A2-presented COL6A3-002 (see table 3 above).

TABLE 4

Features of R4P1D10 alpha chain:

| Start | Stop | Description | Sequence |
| --- | --- | --- | --- |
| 1 | 21 | L segment (TRAV12-2) | MKSLRVLLVILWLQLSWVWSQ (SEQ ID NO: 69) |
| 1 | 113 | V chain (TRAV12-2) | MKSLRVLLVILWLQLSWVWSQQKEVEQNSGPL SVPEGAIASLNCTYSDRGSQSFFWYRQYSGKSP ELIMFIYSNGDKEDGRFTAQLNKASQYVSLLIR DSQPSDSATYLCAVN |
| 48 | 53 | CDR1 | DRGSQS |
| 71 | 72 | CDR2 | IY |
| 110 | 120 | CDR3 | CAVNFHDKIIF |
| 116 | 130 | J segment (TRAJ30) | DKIIFGKGTRLHILP |
| 131 | 272 | Constant region (TRAC) | NIQNPDPAVYQLRDSKSSDKSVCLFTDFDSQTN VSQSKDSDVYITDKTVLDMRSMDFKSNSAVAW SNKSDFACANAFNNSIIPEDTFFPSPESSCDVKL VEKSFETDTNLNFQNLSVIGFRILLLKVAGFNLL MTLRLWSS |

TABLE 5

Features of R4P1D10 beta chain:

| Start | Stop | Description | Sequence |
| --- | --- | --- | --- |
| 1 | 19 | L segment (TRBV9) | MGFRLLCCVAFCLLGAGPV (SEQ ID NO: 70) |
| 1 | 114 | V chain (TRBV9) | MGFRLLCCVAFCLLGAGPVDSGVTQTPKHLIT ATGQRVTLRCSPRSGDLSVYWYQQSLDQGLQ FLIHYYNGEERAKGNILERFSAQQFPDLHSEL NLSSLELGDSALYFCASSV |
| 46 | 50 | CDR1 | SGDLS |
| 68 | 73 | CDR2 | YYNGEE |
| 110 | 122 | CDR3 | CASSVASAYGYTF |
| 118 | 131 | J chain (TRBJ1-2) | YGYTFGSGTRLTVV |
| 132 | 308 | constant region (TRBC1) | EDLNKVFPPEVAVFEPSEAEISHTQKATLVCL ATGFFPDHVELSWWVNGKEVHSGVSTDPQPL KEQPALNDSRYCLSSRLRVSATFWQNPRNHF RCQVQFYGLSENDEWTQDRAKPVTQIVSAEA WGRADCGFTSVSYQQGVLSATILYEILLGKAT LYAVLVSALVLMAMVKRKDF |

Figure 2:
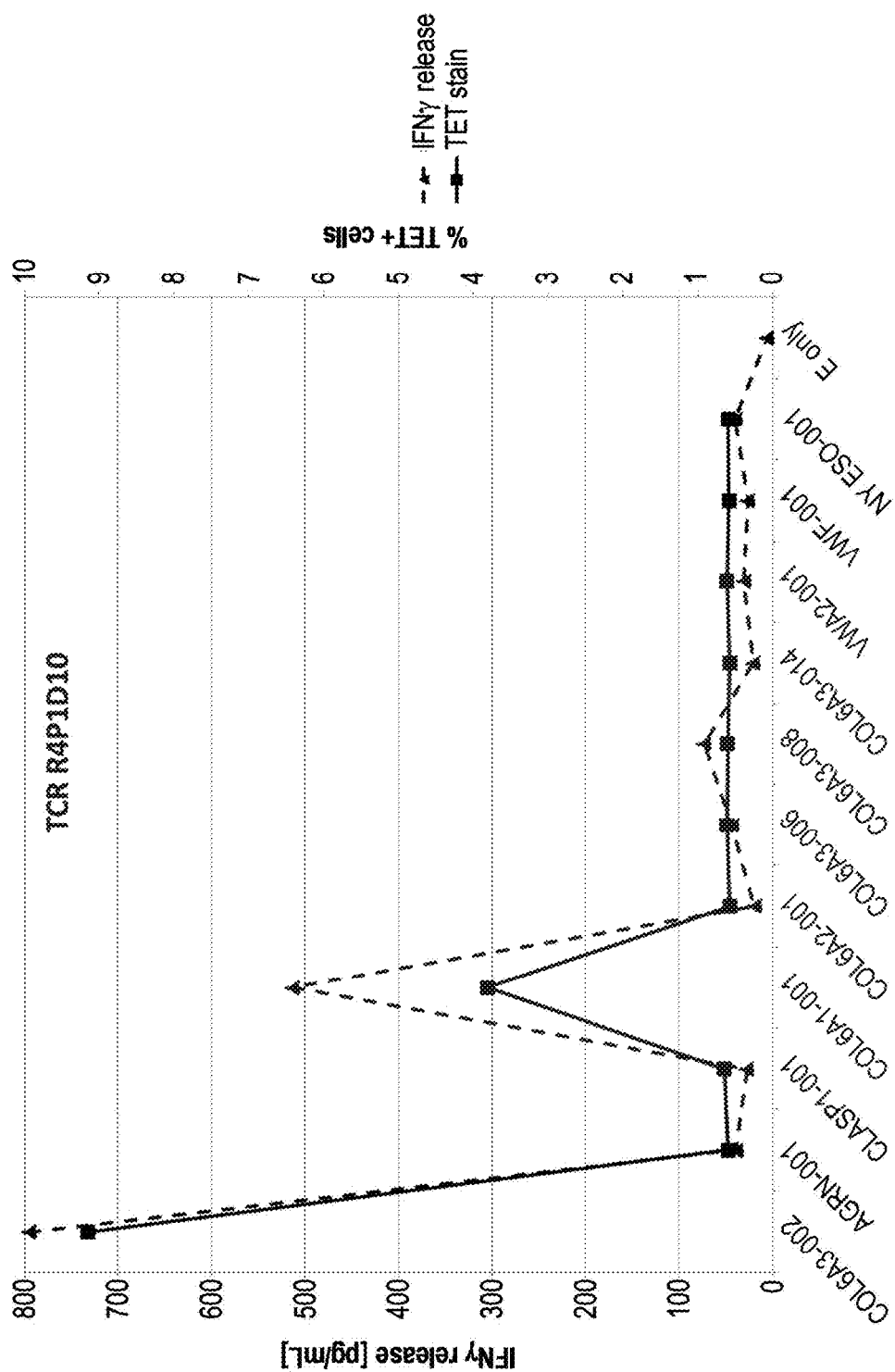
FIG. 2: IFNγ release (left axis) and HLA-A*02/COL6A3-002 tetramer staining (right axis) of human primary CD8+ T-cells of one donor electroporated with alpha and beta chain RNA of TCR R4P1D10 (Table 1), respectively, after co-incubation with K562-A2 target cells loaded with COL6A3-002 peptide (SEQ ID NO:58), homologous but unrelated peptide AGRN-001, CLASP-001, COL6A1-001, COL6A2-001, COL6A3-006, COL6A3-008, COL6A3-014, VWA2-001, VWF-001 (SEQ ID NO:49-57) or NYESO1-001 control peptide (SEQ ID NO:68). Electroporated CD8+ T-cells only (E only) serve as control.

R4P1D10 specifically recognizes COL6A3-002 as human primary CD8+ T-cells re-expressing this TCR release IFNγ upon co-incubation with HLA-A*02+ target cells and bind HLA-A*02 tetramers, respectively, loaded either with COL6A3-002 peptide or alanine and glycine substitution variants of COL6A3-002 (FIG. 1) or different peptides showing high degree of sequence similarity to COL6A3-002 (FIG. 2). NYESO1-001 peptide is used as negative control.

Figure 3:
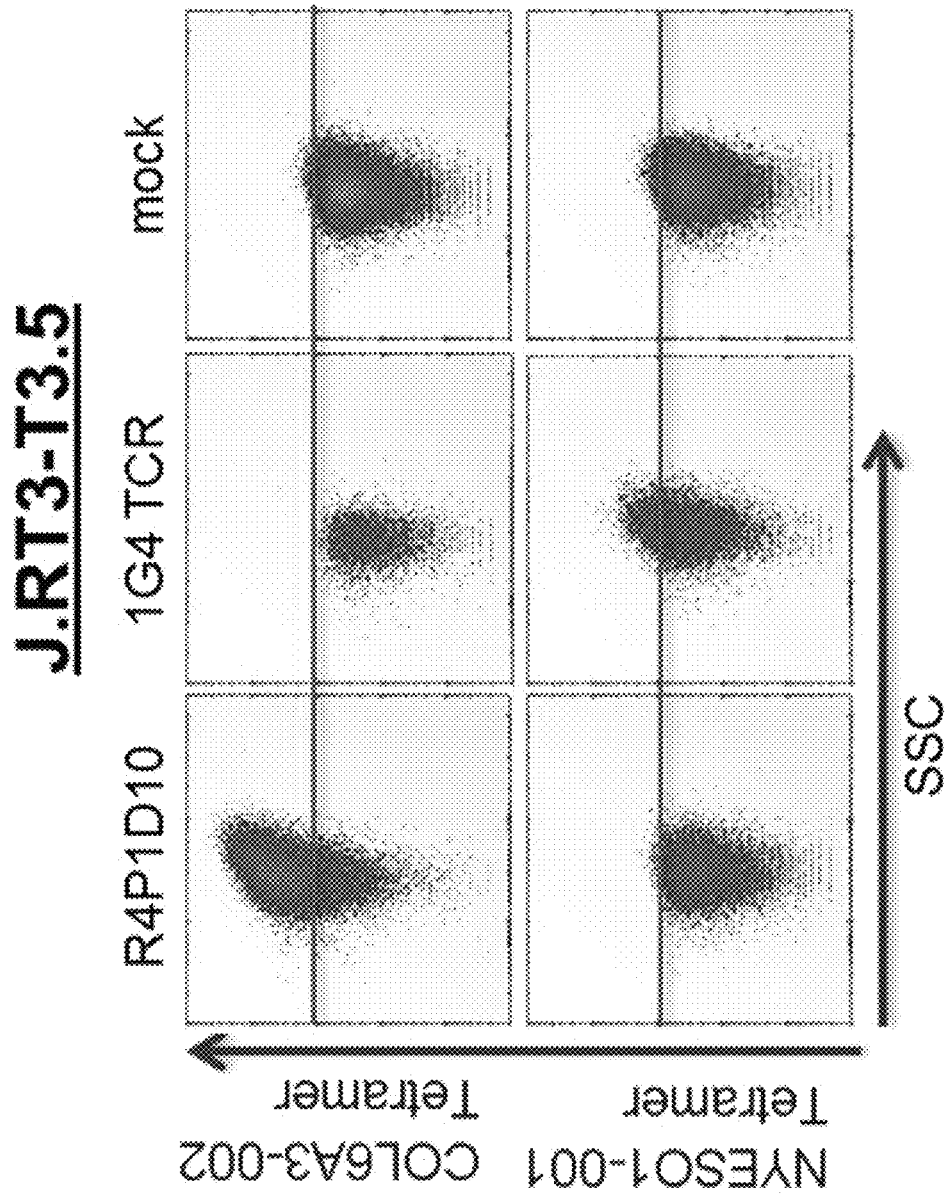
FIG. 3: HLA-A*02/COL6A3-002 tetramer and HLA-A*02/NYESO1-001 tetramer staining, respectively, of J.RT3-T3.5 cells electroporated with alpha and beta chain RNA of TCR R4P1D10 or NYESO1-001-specific control TCR 1G4 (Table 1). Mock electroporated J.RT3-T3.5 cells serve as control.
Figure 4:
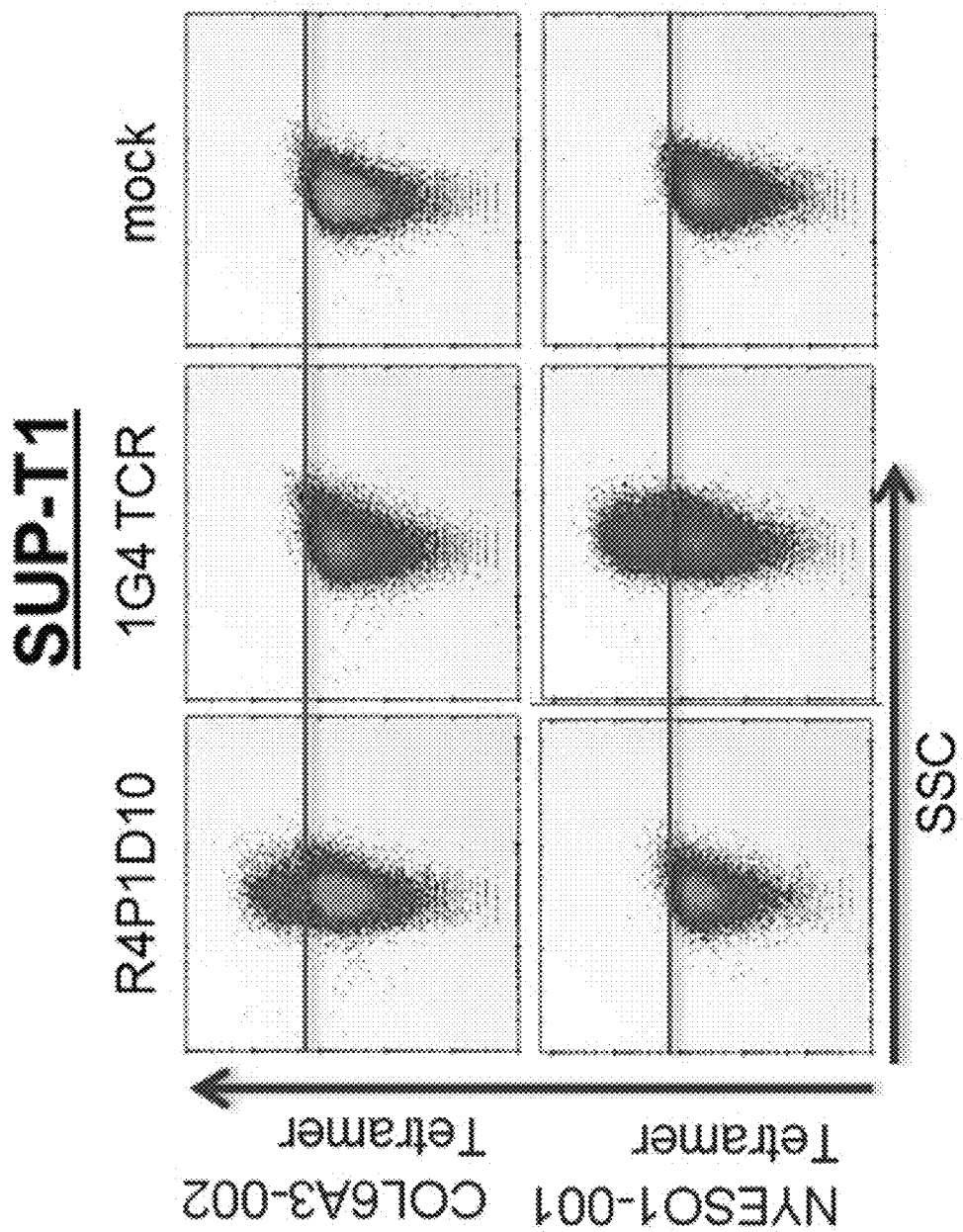
FIG. 4: HLA-A*02/COL6A3-002 tetramer and HLA-A*02/NYESO1-001 tetramer staining, respectively, of SUP-T1 cells electroporated with alpha and beta chain RNA of TCR R4P1D10 or NYESO1-001-specific control TCR 1G4 (Table 1). Mock electroporated SUP-T1 cells serve as control.
Figure 5:
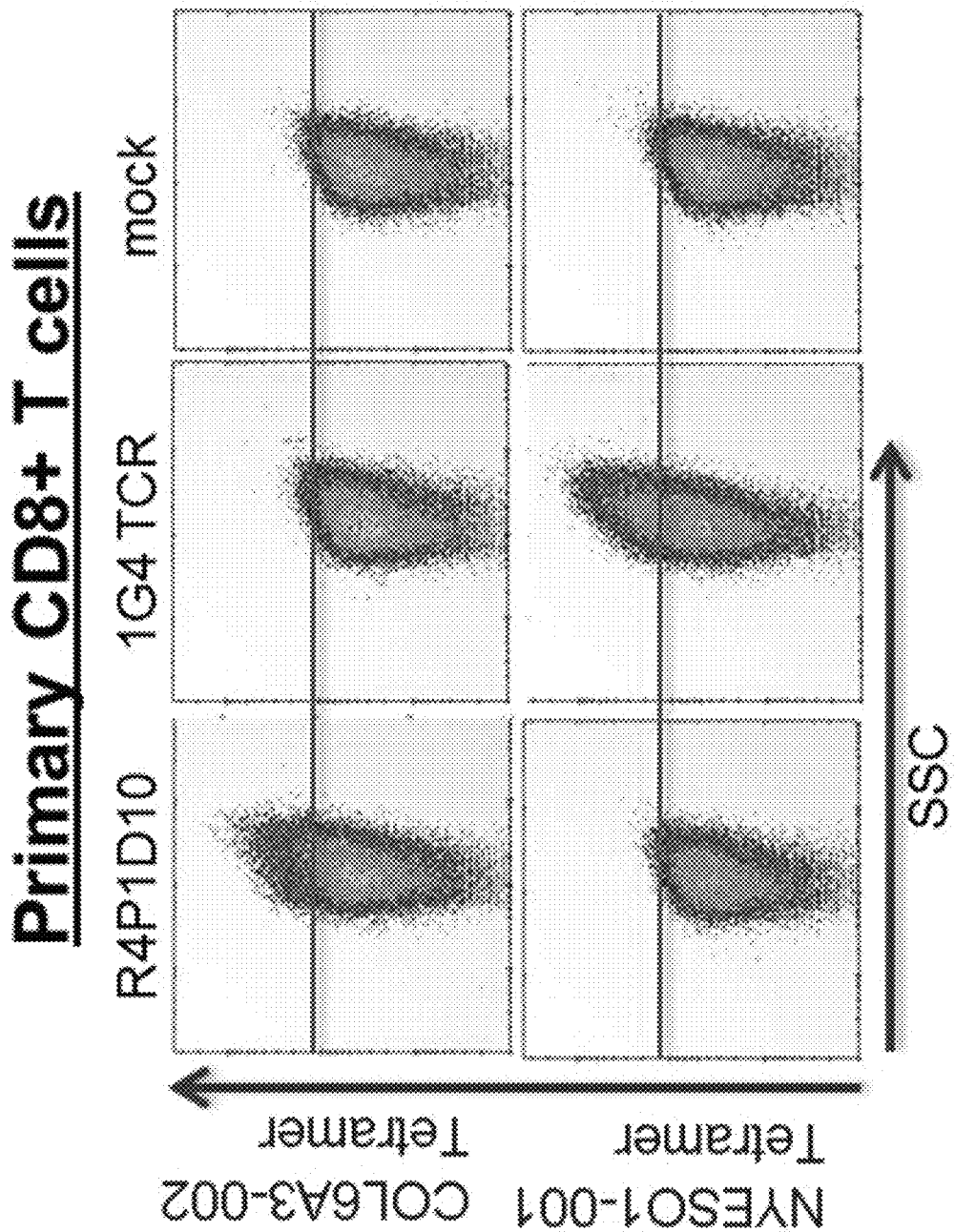
FIG. 5: HLA-A*02/COL6A3-002 tetramer and HLA-A*02/NYESO1-001 tetramer staining, respectively, of human primary CD8+ T-cells of one donor electroporated with alpha and beta chain RNA of TCR R4P1D10 or NYESO1-001-specific control TCR 1G4 (Table 1). Mock electroporated CD8+ T-cells serve as control.

Re-expression of R4P1D10 leads to selective binding of HLA-A*02/COL6A3-002 tetramers but not HLA-A*02/NYESO1-001 tetramers in J.RT3-T3.5 Jurkat cells (FIG. 3), SUP-T1 cells (FIG. 4) and human primary CD8+ T-cells (FIG. 5). For each cell type, re-expression of the NYESO1-001-specific TCR 1G4 and mock expression are used as control.

SPR (Surface Plasmon Resonance) binding analysis for R4P1D10, expressed as soluble TCR according to a previously described method (Willcox B E et al., 1999 Protein Sci., November; 8(11):2418-23), and HLA-A*02/COL6A3-002 complex reveals an affinity of $K_D$=16 µM (Table 3). SPR binding data for 1G4 TCR and HLA-A*02/NYESO1-001 are used as control.

Example 2: T-Cell Receptor R4P3F9

The TCR R4P3F9 alpha and beta chains were cloned as described before, for example, as described in U.S. Pat. No. 8,519,100, which is hereby incorporated by reference in its entirety for said methods. TCR R4P3F9 is restricted towards HLA-A2-presented COL6A3-002 (see table 3 above).

TABLE 6

Features of R4P3F9 alpha chain

| Start | Stop | Description | Sequence |
|---|---|---|---|
| 1 | 21 | L segment (TRAV12-2) | MKSLRVLLVILWLQLSWVWSQ (SEQ ID NO: 71) |
| 1 | 111 | V chain (TRAV12-2) | MKSLRVLLVILWLQLSWVWSQQKEVEQNSGPL SVPEGAIASLNCTYSDRGSQSFFWYRQYSGKSP ELIMFIYSNGDKEDGRFTAQLNKASQYVSLLIR DSQPSDSATYLCA |
| 48 | 53 | CDR1 | DRGSQS |
| 71 | 72 | CDR2 | IY |
| 110 | 123 | CDR3 | CAAYSGAGSYQLTF |
| 113 | 133 | J segment (TRAJ28) | YSGAGSYQLTFGKGTKLSVIP |
| 134 | 274 | Constant region (TRAC) | NIQNPDPAVYQLRDSKSSDKSVCLFTDFDSQTN VSQSKDSDVYITDKTVLDMRSMDFKSNSAVAW SNKSDFACANAFNNSIIPEDTFFPSPESSCDVKL VEKSFETDTNLNFQNLSVIGFRILLLKVAGFNLL MTLRLWSS |

TABLE 7

Features of R4P3F9 beta chain

| Start | Stop | Description | Sequence |
|---|---|---|---|
| 1 | 19 | L segment (TRBV9) | MGFRLLCCVAFCLLGAGPV (SEQ ID NO: 72) |
| 1 | 114 | V chain (TRBV9) | MGFRLLCCVAFCLLGAGPVDSGVTQTPKHLIT ATGQRVTLRCSPRSGDLSVYWYQQSLDQGLQ FLIHYYNGEERAKGNILERFSAQQFPDLHSEL NLSSLELGDSALYFCASSV |
| 46 | 50 | CDR1 | SGDLS |
| 68 | 73 | CDR2 | YYNGEE |
| 110 | 122 | CDR3 | CASSVESSYGYTF |
| 118 | 131 | J chain (TRBJ1-2) | YGYTFGSGTRLTVV |
| 132 | 308 | constant region (TRBC1) | EDLNKVFPPEVAVFEPSEAEISHTQKATLVCL ATGFFPDHVELSWWVNGKEVHSGVSTDPQPL KEQPALNDSRYCLSSRLRVSATFWQNPRNHF RCQVQFYGLSENDEWTQDRAKPVTQIVSAEA WGRADCGFTSVSYQQGVLSATILYEILLGKAT LYAVLVSALVLMAMVKRKDF |

Figure 6:
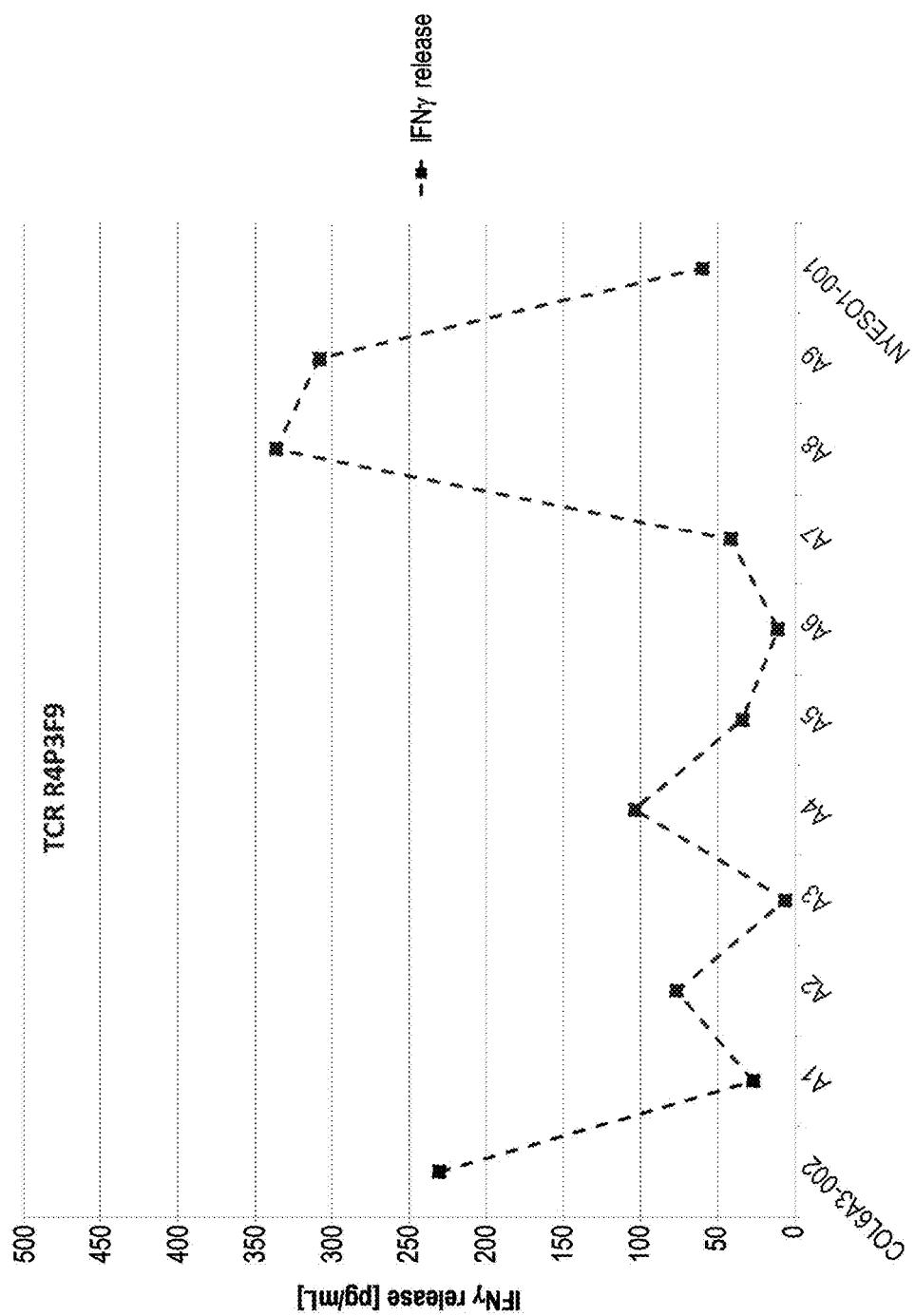
FIG. 6: IFNγ release of human primary CD8+ T-cells of one donor electroporated with alpha and beta chain RNA of TCR R4P3F9 (Table 1), respectively, after coincubation with K562-A2 target cells loaded with COL6A3-002 peptide (SEQ ID NO:58), various COL6A3-002 alanine or glycine substitution variants at positions 1-9 of (SEQ ID NO:59-67), or NYESO1-001 control peptide (SEQ ID NO:68).
Figure 7:
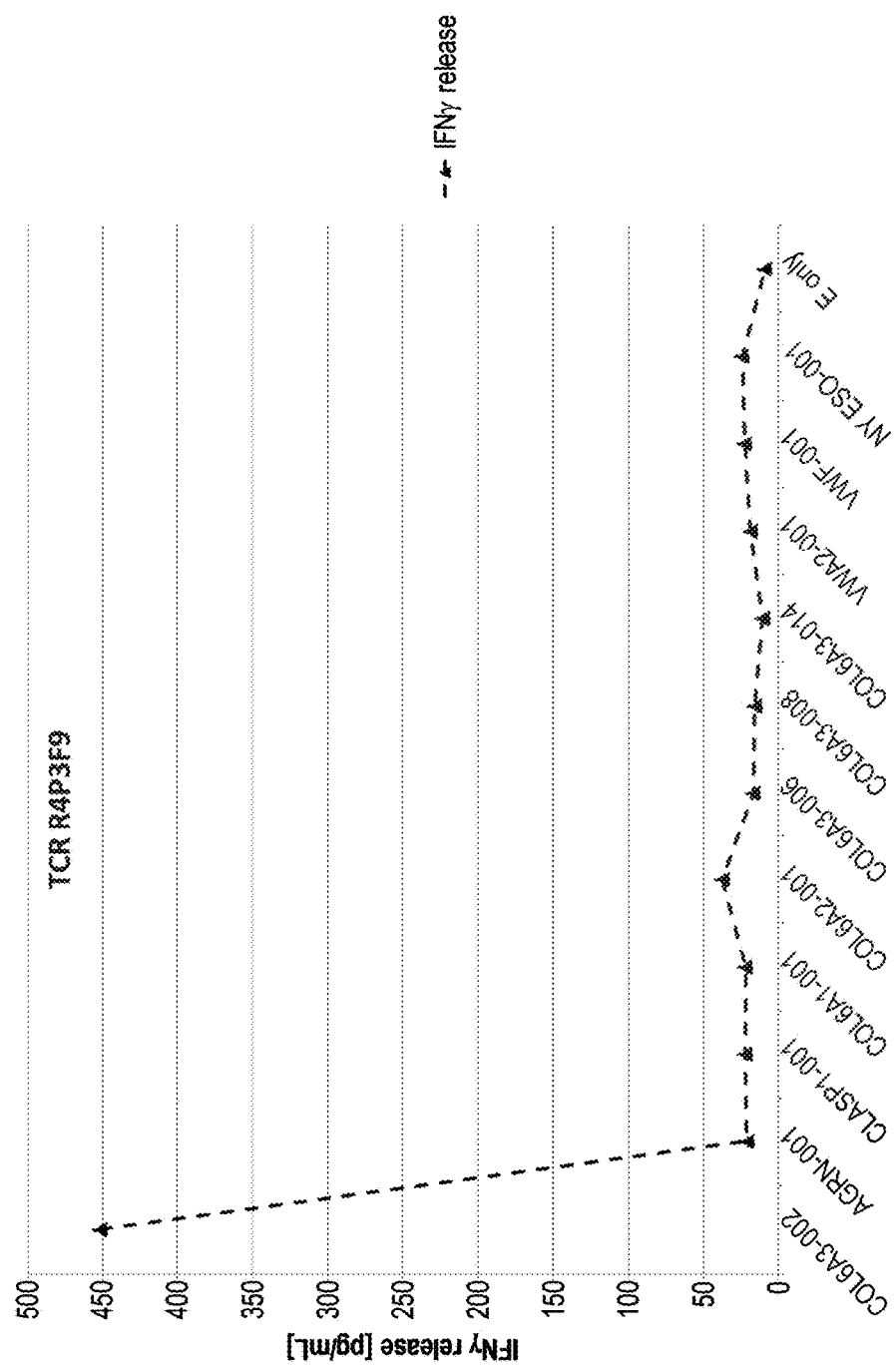
FIG. 7: IFNγ release of human primary CD8+ T-cells of one donor electroporated with alpha and beta chain RNA of TCR R4P3F9 (Table 1), respectively, after coincubation with K562-A2 target cells loaded with COL6A3-002 peptide (SEQ ID NO:58), homologous but unrelated peptide AGRN-001, CLASP-001, COL6A1-001, COL6A2-001, COL6A3-006, COL6A3-008, COL6A3-014, VWA2-001, VWF-001 (SEQ ID NO:49-57) or NYESO1-001 control peptide (SEQ ID NO:68). Mock electroporated CD8+ T-cells (E only) serve as control.

R4P3F9 specifically recognizes COL6A3-002 as human primary CD8+ T-cells re-expressing this TCR release IFNγ upon co-incubation with HLA-A*02+ target cells, respectively, loaded either with COL6A3-002 peptide or alanine and glycine substitution variants of COL6A3-002 (FIG. 6) or different peptides showing high degree of sequence similarity to COL6A3-002 (FIG. 7). NYESO1-001 peptide is used as negative control.

Figure 8:
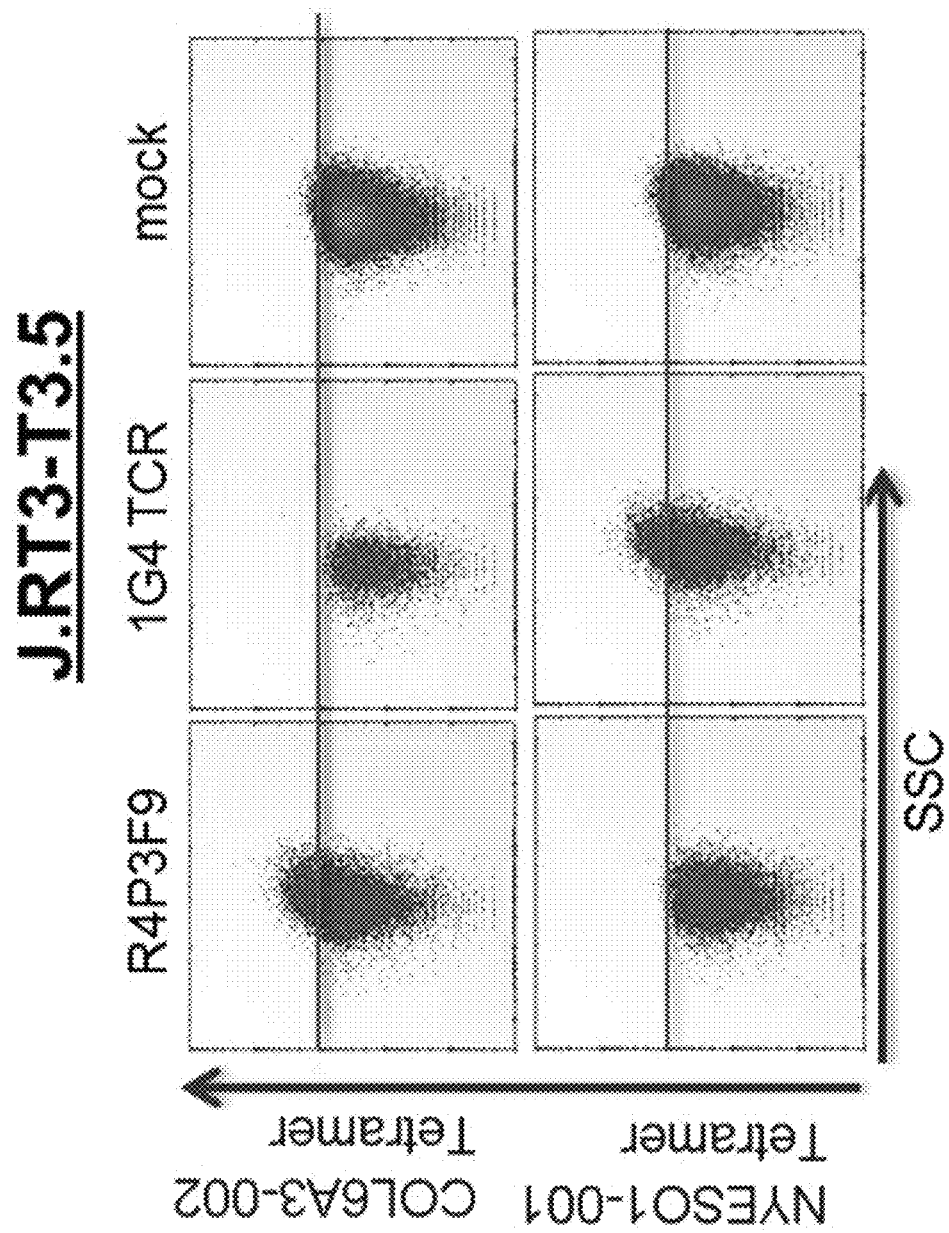
FIG. 8: HLA-A*02/COL6A3-002 tetramer and HLA-A*02/NYESO1-001 tetramer staining, respectively, of J.RT3-T3.5 cells electroporated with alpha and beta chain RNA of TCR R4P3F9 or NYESO1-001-specific control TCR 1G4 (Table 1). Mock electroporated J.RT3-T3.5 cells serve as control.
Figure 9:
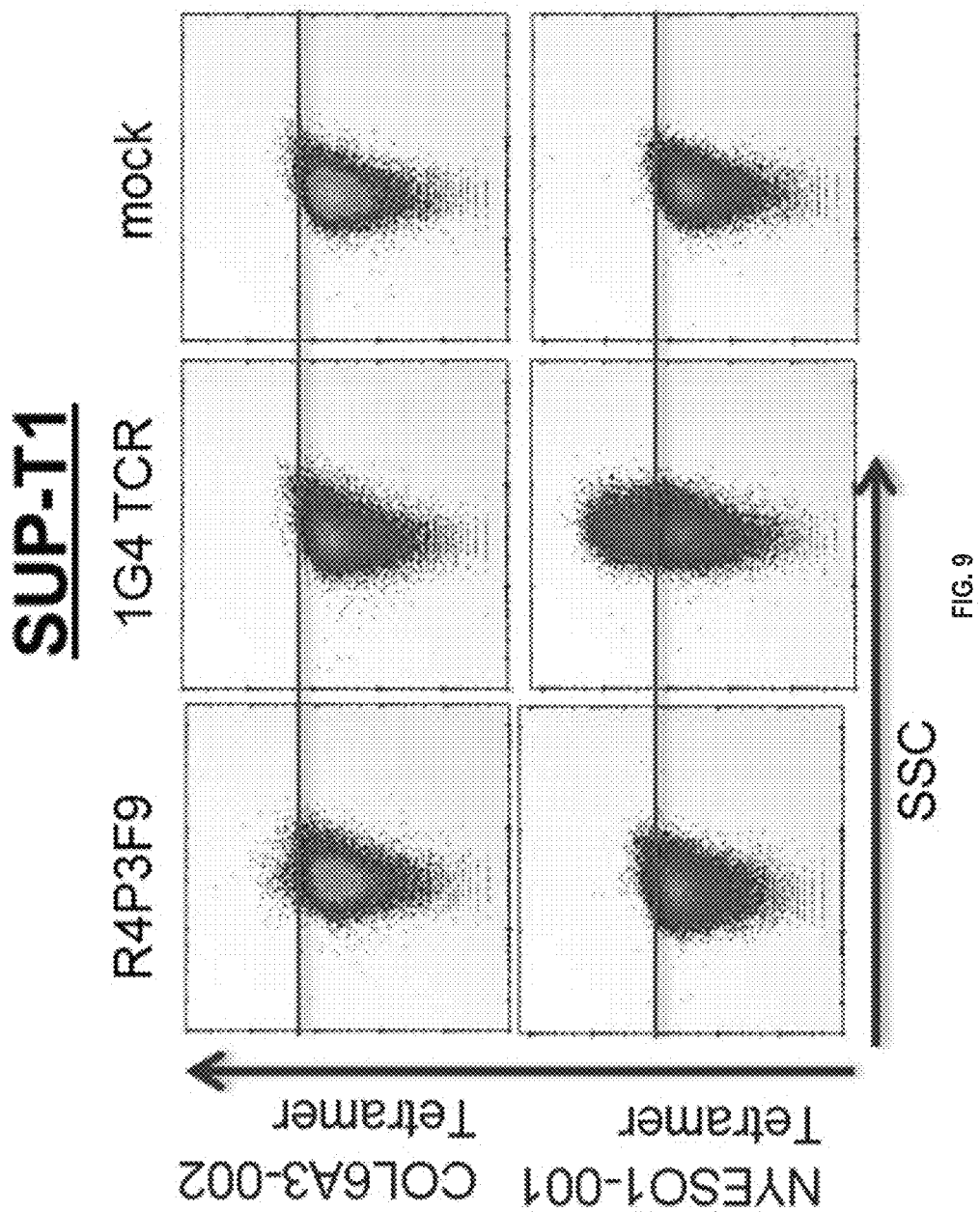
FIG. 9: HLA-A*02/COL6A3-002 tetramer and HLA-A*02/NYESO1-001 tetramer staining, respectively, of SUP-T1 cells electroporated with alpha and beta chain RNA of TCR R4P3F9 or NYESO1-001-specific control TCR 1G4 (Table 1). Mock electroporated SUP-T1 cells serve as control.

Re-expression of R4P3F9 leads to selective binding of HLA-A*02/COL6A3-002 tetramers but not HLA-A*02/NYESO1-001 tetramers in J.RT3-T3.5 Jurkat cells (FIG. 8) and SUP-T1 cells (FIG. 9). For each cell type, re-expression of the NYESO1-001-specific TCR 1G4 and mock expression are used as control.

SPR binding analysis for R4P3F9, expressed as soluble TCR according to a previously described method (Willcox B E et al., 1999 Protein Sci., November; 8(11):2418-23), and HLA-A*02/COL6A3-002 complex reveals an affinity of $K_D$=62 μM (Table 3). SPR binding data for 1G4 TCR and HLA-A*02/NYESO1-001 are used as control.

Example 3: T-Cell Receptor R4P3H3

The TCR R4P3H3 alpha and beta chains were cloned as described before, for example, as described in U.S. Pat. No. 8,519,100, which is hereby incorporated by reference in its entirety. TCR R4P3H3 is restricted towards HLA-A2-presented COL6A3-002 (see table 3 above).

TABLE 8

Features of R4P3H3 alpha chain

| Start | Stop | Description | Sequence |
|---|---|---|---|
| 1 | 21 | L segment (TRAV12-2) | MKSLRVLLVILWLQLSWVWSQ (SEQ ID NO: 73) |
| 1 | 112 | V chain (TRAV12-2) | MKSLRVLLVILWLQLSWVWSQQKEVEQNSGPL SVPEGAIASLNCTYSDRGSQSFFWYRQYSGKSP ELIMFIYSNGDKEDGRFTAQLNKASQYVSLLIR DSQPSDSATYLCAV |
| 48 | 53 | CDR1 | DRGSQS |
| 71 | 72 | CDR2 | IY |
| 110 | 120 | CDR3 | CAVKAGNQFYF |
| 115 | 130 | J segment (TRAJ49) | GNQFYFGTGTSLTVIP |
| 131 | 271 | Constant region (TRAC) | NIQNPDPAVYQLRDSKSSDKSVCLFTDFDSQTN VSQSKDSDVYITDKTVLDMRSMDFKSNSAVAW SNKSDFACANAFNNSIIPEDTFFPSPESSCDVKL VEKSFETDTNLNFQNLSVIGFRILLLKVAGFNLL MTLRLWSS |

TABLE 9

Features of R4P3H3 beta chain

| Start | Stop | Description | Sequence |
|---|---|---|---|
| 1 | 19 | L segment (TRBV7-8) | MGTRLLCWVVLGFLGTDHT (SEQ ID NO: 74) |
| 1 | 115 | V chain (TRBV7-8) | MGTRLLCWVVLGFLGTDHTGAGVSQSPRYK VAKRGQDVALRCDPISGHVSLFWYQQALGQ GPEFLTYFQNEAQLDKSGLPSDRFFAERPEGS VSTLKIQRTQQEDSAVYLCASSL |
| 46 | 50 | CDR1 | SGHVS |
| 68 | 73 | CDR2 | FQNEAQ |
| 111 | 126 | CDR3 | CASSLLTSGGDNEQFF |
| 122 | 135 | J chain (TRBJ2-1) | NEQFFGPGTRLTVL |
| 136 | 314 | constant region (TRBC2) | EDLKNVFPPEVAVFEPSEAEISHTQKATLVCL ATGFYPDHVELSWWVNGKEVHSGVSTDPQP LKEQPALNDSRYCLSSRLRVSATFWQNPRNH FRCQVQFYGLSENDEWTQDRAKPVTQIVSAE AWGRADCGFTSESYQQGVLSATILYEILLGKA TLYAVLVSALVLMAMVKRKDSRG |

Figure 10:
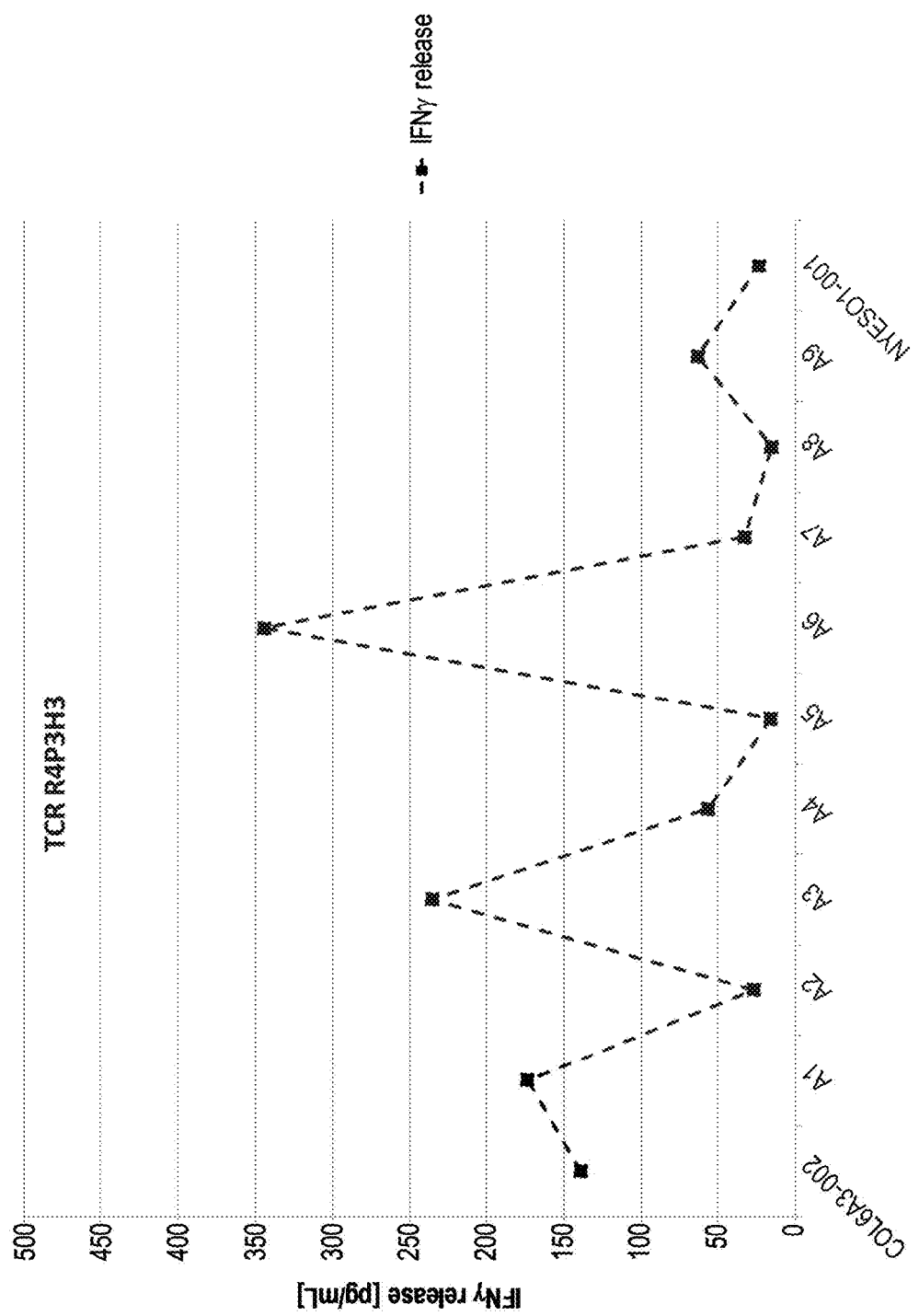
FIG. 10: IFNγ release of human primary CD8+ T-cells of one donor electroporated with alpha and beta chain RNA of TCR R4P3H3 (Table 1), respectively, after co-incubation with K562-A2 target cells loaded with COL6A3-002 peptide (SEQ ID NO:58), various COL6A3-002 alanine or glycine substitution variants at positions 1-9 of (SEQ ID NO:59-67) or NYESO1-001 control peptide (SEQ ID NO:68).
Figure 11:
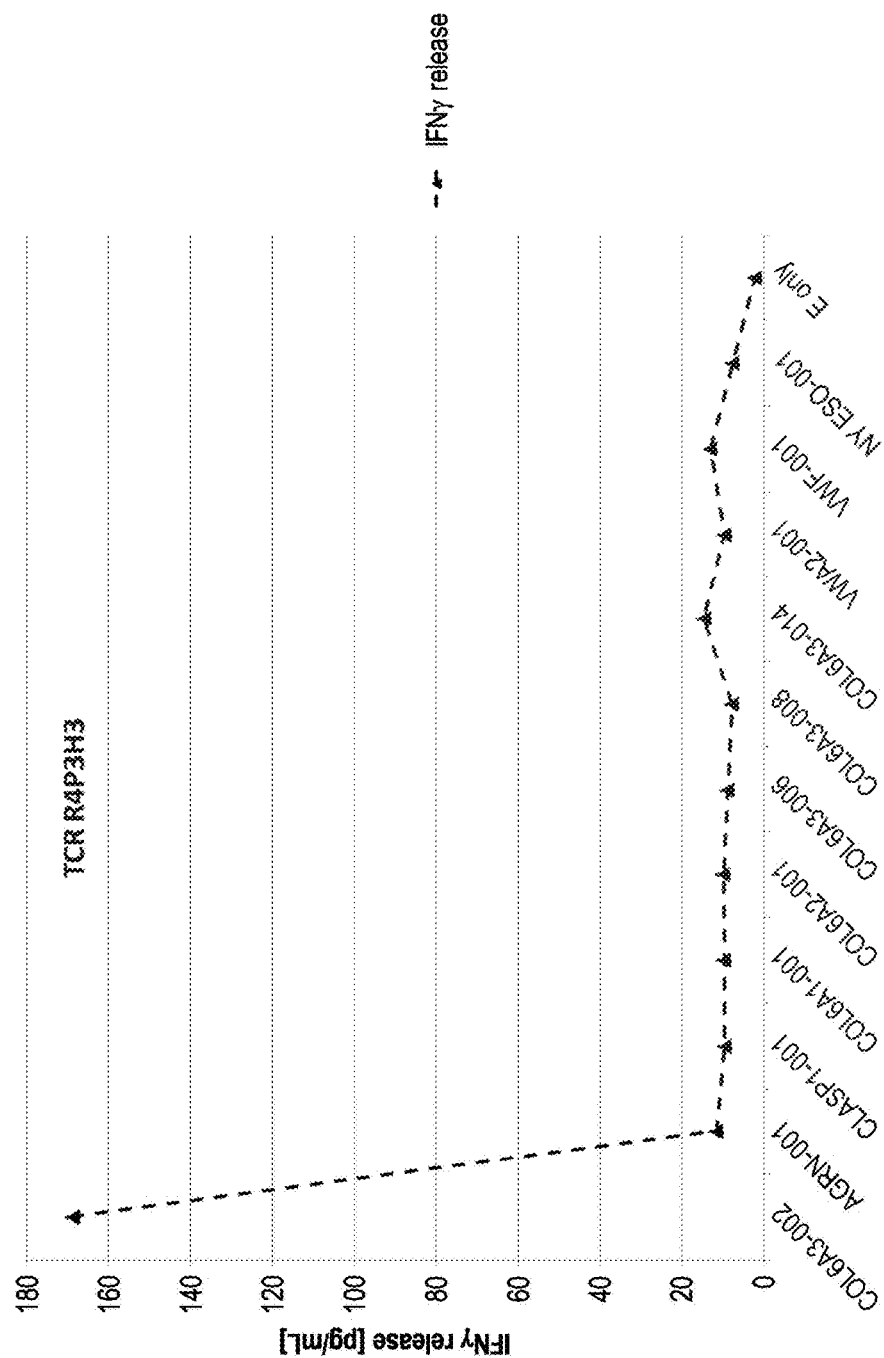
FIG. 11: IFNγ release of human primary CD8+ T-cells of one donor electroporated with alpha and beta chain RNA of TCR R4P3H3 (Table 1), respectively, after co-incubation with K562-A2 target cells loaded with COL6A3-002 peptide (SEQ ID NO:58), homologous but unrelated peptide AGRN-001, CLASP-001, COL6A1-001, COL6A2-001, COL6A3-006, COL6A3-008, COL6A3-014, VWA2-001, VWF-001 (SEQ ID NO:49-57) or NYESO1-001 control peptide (SEQ ID NO:68). Mock electroporated CD8+ T-cells (E only) serve as control.

R4P3H3 specifically recognizes COL6A3-002 as human primary CD8+ T-cells re-expressing this TCR release IFNγ upon co-incubation with HLA-A*02+ target cells, respectively, loaded either with COL6A3-002 peptide or alanine and glycine substitution variants of COL6A3-002 (FIG. 10) or different peptides showing high degree of sequence similarity to COL6A3-002 (FIG. 11). NYESO1-001 peptide is used as negative control.

Re-expression of R4P3H3 leads to selective binding of HLA-A*02/COL6A3-002 tetramers but not HLA-A*02/ NYESO1-001 tetramers in SUP-T1 cells (FIG. 12). Re-expression of the NYESO1-001-specific TCR 1G4 and mock expression are used as control.

SPR binding analysis for R4P3H3, expressed as soluble TCR according to a previously described method (Willcox B E et al., 1999 Protein Sci., November; 8(11):2418-23), and HLA-A*02/COL6A3-002 complex reveals an affinity of $K_D$=102 μM (Table 3). SPR binding data for 1G4 TCR and HLA-A*02/NYESO1-001 are used as control.

The invention claimed is:

1. A method of treating an HLA-A*02-positive patient who has cancer, comprising administering to the patient a population of transformed CD8+ T cells expressing at least one vector encoding a T cell receptor (TCR) on the cell surface,
wherein the TCR comprises:
a CDR1α chain comprising the amino acid sequence of SEQ ID NO: 1, a CDR2α chain comprising the amino acid sequence of SEQ ID NO: 2, and a CDR3α chain comprising the amino acid sequence of SEQ ID NO: 3 and a CDR1β chain comprising the amino acid sequence of SEQ ID NO: 7, a CDR2β chain comprising the amino acid sequence of SEQ ID NO: 8, and a CDR3β chain comprising the amino acid sequence of SEQ ID NO: 9; or
a CDR1α chain comprising the amino acid sequence of SEQ ID NO: 13, a CDR2α chain comprising the amino acid sequence of SEQ ID NO: 14, and a CDR3α chain comprising the amino acid sequence of SEQ ID NO: 15 and a CDR1β chain comprising the amino acid sequence of SEQ ID NO: 19, a CDR2β chain comprising the amino acid sequence of SEQ ID NO: 20, and a CDR3β chain comprising the amino acid sequence of SEQ ID NO: 21; or a CDR1α chain comprising the amino acid sequence of SEQ ID NO: 25, a CDR2α chain comprising the amino acid sequence of SEQ ID NO: 26, and a CDR3α chain comprising the amino acid sequence of SEQ ID NO: 27 and a CDR1β chain comprising the amino acid sequence of SEQ ID NO: 31, a CDR2β chain comprising the amino acid sequence of SEQ ID NO: 32, and a CDR3β chain comprising the amino acid sequence of SEQ ID NO: 33;

and wherein the TCR binds to a peptide consisting of the amino acid sequence of FLLDGSANV (SEQ ID NO: 58) in complex with HLA-A*02, wherein the cancer is a FLLDGSANV (SEQ ID NO: 58)/HLA-A*02 complex-positive cancer selected from the group consisting of gastrointestinal cancer, gastric cancer, breast cancer, colorectal cancer, esophageal cancer, liver cancer, lung cancer, melanoma, non-Hodgkin lymphoma, ovarian cancer, pancreatic cancer, cholangiocellular carcinoma, gallbladder cancer, head and neck squamous cell carcinoma, uterine and endometrial cancer, and urinary bladder cancer.

2. The method of claim 1, wherein the population of transformed cells are produced by a method comprising
isolating a cell from a subject,
transforming the cell with at least one vector encoding the TCR to produce a transformed cell, and
expanding the transformed cell to produce the population of transformed cells.

3. The method of claim 2, wherein the subject is a healthy donor.

4. The method of claim 1, wherein the TCR comprises one of the following α chain/β chain pairs:
an α chain consisting of the amino acid sequences of SEQ ID NO: 6 and a β chain consisting of the amino acid sequences of SEQ ID NO: 12;
an α chain consisting of the amino acid sequences of SEQ ID NO: 18 and a β chain consisting of the amino acid sequences of SEQ ID NO: 24; or
α chain consisting of the amino acid sequences of SEQ ID NO: 30 and a β chain consisting of the amino acid sequences of SEQ ID NO: 36.

5. The method of claim 1, wherein the population of transformed cells are administered in the form of a pharmaceutical composition.

6. The method of claim 5, wherein the pharmaceutical composition comprises a chemotherapeutic agent selected from the group consisting of asparaginase, busulfan, carboplatin, cisplatin, daunorubicin, doxorubicin, fluorouracil, gemcitabine, hydroxyurea, methotrexate, paclitaxel, rituximab, vinblastine, and vincristine.

7. The method of claim 1, wherein the cancer is gastrointestinal cancer or gastric cancer.

8. A method of eliciting an antigen-specific CD8+ cytotoxic T cell immune response in an HLA-A*02-positive patient who has cancer, comprising administering to the patient a population of transformed CD8+ T cells expressing at least one vector encoding a T cell receptor (TCR) on the cell surface,
wherein the TCR comprises:
a CDR1α chain comprising the amino acid sequence of SEQ ID NO: 1, a CDR2α chain comprising the amino acid sequence of SEQ ID NO: 2, and a CDR3α chain comprising the amino acid sequence of SEQ ID NO: 3 and a CDR1β chain comprising the amino acid sequence of SEQ ID NO: 7, a CDR2β chain comprising the amino acid sequence of SEQ ID NO: 8, and a CDR3β chain comprising the amino acid sequence of SEQ ID NO: 9; or a CDR1α chain comprising the amino acid sequence of SEQ ID NO: 13, a CDR2α chain comprising the amino acid sequence of SEQ ID NO: 14, and a CDR3α chain comprising the amino acid sequence of SEQ ID NO: 15 and a CDR1β chain comprising the amino acid sequence of SEQ ID NO: 19, a CDR2β chain comprising the amino acid sequence of SEQ ID NO: 20, and a CDR3β chain comprising the amino acid sequence of SEQ ID NO: 21; or a CDR1α chain comprising the amino acid sequence of SEQ ID NO: 25, a CDR2α chain comprising the amino acid sequence of SEQ ID NO: 26, and a CDR3α chain comprising the amino acid sequence of SEQ ID NO: 27 and a CDR1β chain comprising the amino acid sequence of SEQ ID NO: 31, a CDR2β chain comprising the amino acid sequence of SEQ ID NO: 32, and a CDR3β chain comprising the amino acid sequence of SEQ ID NO: 33;

and wherein the TCR binds to a peptide consisting of the amino acid sequence of FLLDGSANV (SEQ ID NO: 58) in complex with HLA-A*02, wherein the cancer is a FLLDGSANV (SEQ ID NO: 58)/HLA-A*02 complex-positive cancer selected from the group consisting of gastrointestinal cancer, gastric cancer, breast cancer, colorectal cancer, esophageal cancer, liver cancer, lung cancer, melanoma, non-Hodgkin lymphoma, ovarian cancer, pancreatic cancer, cholangiocellular carcinoma, gallbladder cancer, head and neck squamous cell carcinoma, uterine and endometrial cancer, and urinary bladder cancer.

9. The method of claim 7, wherein the population of transformed cells are produced by a method comprising
isolating a cell from a subject,
transforming the cell with at least one vector encoding the TCR to produce a transformed cell, and
expanding the transformed cell to produce the population of transformed cells.

10. The method of claim 8, wherein the subject is a healthy donor.

11. The method of claim 7, wherein the TCR comprises one of the following α chain/β chain pairs:
an α chain consisting of the amino acid sequences of SEQ ID NO: 6 and a β chain consisting of the amino acid sequences of SEQ ID NO: 12;
an α chain consisting of the amino acid sequences of SEQ ID NO: 18 and a β chain consisting of the amino acid sequences of SEQ ID NO: 24; or
α chain consisting of the amino acid sequences of SEQ ID NO: 30 and a β chain consisting of the amino acid sequences of SEQ ID NO: 36.

12. The method of claim 7, wherein the population of transformed cells are administered in the form of a pharmaceutical composition.

13. The method of claim 11, wherein the pharmaceutical composition comprises a chemotherapeutic agent selected from the group consisting of asparaginase, busulfan, carboplatin, cisplatin, daunorubicin, doxorubicin, fluorouracil, gemcitabine, hydroxyurea, methotrexate, paclitaxel, rituximab, vinblastine, and vincristine.

14. The method of claim 1, wherein the TCR comprises a complementary determining region (CDR) 3α chain consists of one of the following CDR3α chain/CDR3β chain pairs:
- a CDR3α chain consisting of the amino acid sequence of SEQ ID NO: 3 and a CDR3β chain consisting of the amino acid sequence of SEQ ID NO: 9;
- a CDR3α chain consisting of the amino acid sequence of SEQ ID NO: 15 and a CDR3β chain consisting of the amino acid sequence of SEQ ID NO: 21; or
- a CDR3α chain consisting of the amino acid sequence of SEQ ID NO: 27 and a CDR3β chain consisting of the amino acid sequence of SEQ ID NO: 33.

15. The method of claim 7, wherein the TCR comprises a complementary determining region (CDR) 3α chain consists of one of the following CDR3α chain/CDR3β chain pairs:
- a CDR3α chain consisting of the amino acid sequence of SEQ ID NO: 3 and a CDR3β chain consisting of the amino acid sequence of SEQ ID NO: 9;
- a CDR3α chain consisting of the amino acid sequence of SEQ ID NO: 15 and a CDR3β chain consisting of the amino acid sequence of SEQ ID NO: 21; or
- a CDR3α chain consisting of the amino acid sequence of SEQ ID NO: 27 and a CDR3β chain consisting of the amino acid sequence of SEQ ID NO: 33.

16. The method of claim 1, wherein the TCR comprises:
- a CDR1α chain comprising SEQ ID NO: 1;
- a CDR2α chain comprising SEQ ID NO: 2;
- a CDR3α chain comprising SEQ ID NO: 3;
- a CDR1β chain comprising SEQ ID NO: 7;
- a CDR2β chain comprising SEQ ID NO: 8; and
- a CDR3β chain comprising SEQ ID NO: 9.

17. The method of claim 7, wherein the TCR comprises:
- a CDR1α chain comprising SEQ ID NO: 1;
- a CDR2α chain comprising SEQ ID NO: 2;
- a CDR3α chain comprising SEQ ID NO: 3;
- a CDR1β chain comprising SEQ ID NO: 7;
- a CDR2β chain comprising SEQ ID NO: 8; and
- a CDR3β chain comprising SEQ ID NO: 9.

18. The method of claim 1, wherein the TCR comprises:
- a CDR1α chain consisting of SEQ ID NO: 1;
- a CDR2α chain comprising of SEQ ID NO: 2;
- a CDR3α chain comprising SEQ ID NO: 3;
- a CDR1β chain consisting of SEQ ID NO: 7;
- a CDR2β chain consisting of SEQ ID NO: 8; and
- a CDR3β chain comprising SEQ ID NO: 9.

19. The method of claim 7, wherein the TCR comprises:
- a CDR1α chain consisting of SEQ ID NO: 1;
- a CDR2α chain comprising of SEQ ID NO: 2;
- a CDR3α chain comprising SEQ ID NO: 3;
- a CDR1β chain consisting of SEQ ID NO: 7;
- a CDR2β chain consisting of SEQ ID NO: 8; and
- a CDR3β chain comprising SEQ ID NO: 9.

20. The method of claim 17, wherein the TCR is a single chain TCR.

21. The method of claim 19, wherein the cancer is lung cancer.

22. The method of claim 18, wherein the TCR is a single chain TCR.

23. The method of claim 21, wherein the cancer is lung cancer.

24. The method of claim 17, wherein the TCR is a single chain TCR.

* * * * *